United States Patent [19]
Anderson et al.

[11] Patent Number: 5,824,489
[45] Date of Patent: Oct. 20, 1998

[54] IN VITRO METHOD FOR OBTAINING AN ISOLATED POPULATION OF MAMMALIAN NEURAL CREST STEM CELLS

[75] Inventors: David J. Anderson, Altadena; Derek L. Stemple, Pasadena, both of Calif.

[73] Assignee: California Institute of Technology, Pasadena, Calif.

[21] Appl. No.: 290,229

[22] Filed: Aug. 15, 1994

Related U.S. Application Data

[63] Continuation of Ser. No. 969,088, Oct. 29, 1992, abandoned, which is a continuation-in-part of Ser. No. 920,617, Jul. 27, 1992, abandoned.

[51] Int. Cl.$^6$ .................................................. C12N 5/00
[52] U.S. Cl. .................. 435/7.21; 435/325; 435/375; 435/377; 435/378; 435/395; 435/402
[58] Field of Search .......................... 435/240.2, 240.21, 435/240.23, 29, 7.21, 325, 375, 377, 378, 395, 402, 240.243; 935/89

[56] References Cited

U.S. PATENT DOCUMENTS

| | | | |
|---|---|---|---|
| 4,705,751 | 11/1987 | Mosher | 435/68 |
| 4,707,448 | 11/1987 | Major | 435/240.25 |
| 5,061,620 | 10/1991 | Tsukamota et al. | 435/7.21 |
| 5,087,570 | 2/1992 | Weissman et al. | 435/240.1 |

OTHER PUBLICATIONS

Lo, L.-C., et al., "V-myc Immortalization of Early Rat Neural Crest Cells Yields a Clonal Cell Line Which Generates both Glial and Adrenergic Progenitor Cells", *Developmental Biology* 145:139–153 (1991).
Stemple, D. L., et al., "A Schwann cell antigen recognized by monoclonal antibody 217c is the rat low–affinity nerve growth factor receptor", *Neuroscience Letters* 124:57–60 (1991).
Murphy, M., et al., "Generation of sensory neurons is stimulated by leukemia inhibitory factor", *Proc. Natl. Acad. Sci. USA* 88:3498–3501 (1991).
Morrison–Graham, K., et al., "Extracellular matrix from Normal but Not Steel Mutant Mice Enhances Melanogenesis in Cultured Mouse Neural Crest Cells", *Developmental Biology* 139:299–307 (1990).
Boisseau, S., et al., "Mammalian neuronal differentiation: early expression of a neuronal phenotype from mouse neural crest cells in a chemically defined culture medium", *Development* 106:665–674 (1989).
Smith–Thomas, L. C., et al., "Expression of Schwann cell markers by mammalian neural crest cells in vitro", *Development* 105:251–262 (1989).
Deville, F. S.S.C., et al., "Developmental potentialities of cells derived from the truncal neural crest in clonal cultures", *Developmental Brain Research* 66:1–10 (1992).
Baroffio, A., et al., "Common precursors for neural and mesectodermal derivatives in the cephalic neural crest", *Development* 112:301–305 (1991).

Baroffio, A., et al., "Clone–forming ability and differentiation potential of migratory neural crest cells", *Proc. Natl. Acad. Sci. USA* 85:5325–5329 (1988).
Dupin, E., et al., "Schwann–cell differentiation in clonal cultures of the neural crest, as evidence by the anti–Schwann cell myelin protein monoclonal antibody", *Proc. Natl. Acad. Sci. USA* 87:1119–1123 (1990).
Cohen, A. M., et al., "A Clonal Approach to the Problem of Neural Crest Determination", *Developmental Biology* 46:262–280 (1975).
Sieber–Blum, M., et al., "Clonal Analysis of Quail Neural Crest Cells: They are Pluripotent and Differentiate in Vitro in the Absence of Noncrest Cells", *Developmental Biology* 80:96–106 (1980).
Duff, R.S., et al., "In Vitro Analysis of Progenitor Cell Patterns in Dorsal Root and Sympathetic Gangila of the Quail Embryo", *Developmental Biology* 147:451–459 (1991).
Bronner–Fraser, M., et al., "Developmental Potential of Avian Trunk Neural Crest Cells In Situ", *Neuron* 3:755–766 (1989).
Bronner–Fraser, M., et al., "Cell lineage analysis reveals multipotency of some avian neural crest cells", *Nature* 355:161–164 (1988).
Fraser, S. E., et al., "Migrating neural crest cells in the trunk of the avian embryo are multipotent", *Development* 112:913–920 (1991).
Frank, E., et al., "Lineage of neurons and glia in chick dorsal root ganglia: analysis in vivo with a recombinant retrovirus", *Development* 111:895–908 (1991).
Le Douarin, N. M., "Cell Line Segregation During Peripheral Nervous System Ontogeny", *Science* 231:1515–1522 (1986).

(List continued on next page.)

*Primary Examiner*—Marianne P. Allen
*Assistant Examiner*—Patricia A. Duffy
*Attorney, Agent, or Firm*—Flehr, Hohbach, Test, Albritton & Herbert LLP; Richard F. Trecartin; Robin M. Silva

[57] ABSTRACT

The invention includes methods for the isolation and clonal propagation of mammalian neural stem cells. The methods employ a novel separation and culturing regimen and bioassays for establishing the generation of neural stem cell derivatives. These methods result in the production of non-transformed neural stem cells and their progeny. The invention demonstrates, at the clonal level, the self regeneration and asymmetrical division of mammalian neural stem cells for the first time in feeder cell-independent cultures. Lineage restriction is demonstrated within a developing clone and is shown to be sensitive to the local environment. Multipotent neural stem cells cultured on a mixed substrate of poly-D-lysine and fibronectin generate PNS neurons and glia, but on fibronectin alone the stem cells generate PNS glia but not neurons. The neurogenic potential of the stem cells, while not expressed, is maintained over time on fibronectin. The invention further includes transplantation assays which allow for the identification of mammalian neural stem cells from various tissues. It also includes methods for transplanting mammalian neural stem cells and/or neural or glial progenitors into mammals.

21 Claims, 16 Drawing Sheets

OTHER PUBLICATIONS

Gorham, J. D., et al., "The expression of the neuronal intermediate filament protein peripherin in the rat embryo", *Developmental Brain Research* 57:235–248 (1990).

Portier, M. M., et al., "Regulation of Peripherin in Mouse Neuroblastoma and Rat PC 12 Pheochromocytoma Cell Lines", *Dev. Neurosci.* 6:215–226 (1983/84).

Portier, M. M., et al., "Periherin, a New Member of the Intermediate Filament Protein Family", *Dev. Neurosci.* 6:335:344 (1983/84).

Parysek, L. M., et al., "Distribution of a Novel 57 kDa Intermediate Filament (IF) Protein in the Nervous System", *The Journal of Neuroscience* 8:555–563 (1988).

Parysek, L. M., et al., "A Type III Intermediate Filament Gene Is Expressed in Mature Neurons", *Neuron* 1:395–401 (1988).

Anderson, D. J., et al., "A Bipotential Neuroendocrine Precursor Whose Choice of Cell Fate Is Determined by NGF and Glucocorticoids", *Cell* 47:1079–1090 (1986).

Birren, S. J., et al., "A v–myc–Immortalized Sympathoadrenal Progenitor Cell Line in Which Neuronal Differentiation Is Initiated by FGF but Not NGF", *Neuron* 4:189–201 (1990.

Potten, C. S., et al., "Stem Cells: attributes, cycles, spirals, pitfalls and uncertainties Lessons for and from the Crypt", *Development* 110:1001–1020 (1990).

Hail, P. A., et al., "Stem cells: the generation and maintenance of cellular diversity", *Development* 106:619–633 (1989).

Raff, M. C., et al., "A glial progenitor cell that develops in vitro into an astrocyte or an oligodendrocyte depending on culture medium", *Nature* 303:390–396 (1983).

Jessen, K. R., et al., "Three markers of adult non–myelin–forming Schwann cells, 217c(Ran–1), A5E3 and GFAP: development and regulation by neuron–Schwann cell interactions", *Development* 109:91–103 (1990).

Porter, S., et al., "Schwann Cells Stimulated to Proliferate in the Absence of Neurons Retain Full Functional Capability", *The Journal of Neuroscience* 6:3070–3078 (1986).

Brockes, J. P., et al., "Studies on Cultured Rat Schwann Cells. I. Establishment of Purified Populations From Cultures of Peripheral Nerve", *Brain Research* 165:105–118 (1979).

Reynolds, B. A., et al., Generation of Neurons and Astrocytes from Isolated Cells of the Adult Mammalian Central Nervous System, *Science* 255:1707–1710 (1992).

Huszar, D., et al., "Migration and proliferation of cultured neural crest cells in W mutant neural crest chimeras", *Development* 112:131–141 (1991).

Anderson, D. J., "The Neural Crest Cell Lineage Problem: Neuropoiesis", *Neuron* 3:1–12 (1989).

Dodd, J., et al., "Spatial Regulation of Axonal Glycoprotein Expression on Subsets of Embryonic Spinal Neurons", *Neuron* 1:105–116 (1988).

Johnson, D., et al., "Expression and Structure of the Human NGF Receptor", *Cell* 47:545–554 (1986).

Chandler, C. E., et al., "A Monoclonal Antibody Modulates the Interaction Nerve Growth Factor with PC12 Cells", *The Journal of Biological Chemistry* 259:6882–6889 (1984).

Chao, M. V., et al., "Gene Transfer and Molecular Cloning of he Human NGF Receptor", *Science* 232:518–521 (1986).

Radeke, M. J., et al., "Gene transfer and molecular cloning of the rat nerve growth factor receptor", *Nature* 325:593–597 (1987).

Weskanp, G., et al., "Evidence That Biological Activity of NGF Is Mediated through a Novel Subclass of High Affinity Receptors", *Neuron* 6:649–663 (1991).

Lendahl, U., et al., "CBS Stem Cells Express a New Class of Intermediate Filament Protein", *Cell* 60:585–595 (1990).

Hockfield, S., et al., "Identification of Major Cell Classes in the Developing Mammalian Nervous System", *The Journal of Neuroscience* 5:3310–3328 (1985).

Friedman, B., et al., "Monoclonal Antibody Rat 401 Recognized Schwann Cells in Mature and Developing Peripheral Nerve", *The Journal of Comparative Neurology* 295:43–51 (1990).

GIBCO–BRL Catalog (1992) pp. 1 and 121.

Soneto et al (1987) In "Neurochemistry: A practical approach", (A.J. Turner et al, eds), IRL Press, Washington DC, pp. 52–55.

Boehringer–Mannheim Biochemicals catalog (1991) pp. 549 & 280–281.

Calbiochem Biochemical/Immunochemical Catalog (1990–1991) pp. 280–284.

Alberts et al (1989) "Molecular Biology of the Cell", Garland Publishing, Inc., New York, pp. 159–163.

Reynolds, B. A., et al., "EGF– and TGFα–Responsive Striatal Embryonic Progenitor Cells Produce Both Neurons and Astrocytes", *Soc. Neurosc. Abst.,* 15:1147 (1990).

Reynolds, B. A., et al., "A Non–Transformed, Growth Factor–Dependent Stem Cell Line Derived from the Embryonic Mouse CNS Produces Neurons, Astrocytes and Oligodendrocytes", *Current Contents/Life Sciences, Excerpta Medica (EMBASE) and Neuroscience Abstracts,* 4(3):208 (1992).

Bartlett, P. E., et al., "Immortalization of mouse neural precursor cells by the c–myc oncogene", *Proc. Natl. Acad. Sci. USA,* 85:3255–3259 (1988).

Bernard, O., et al., "Role of the c–myc and the N–myc Proto–Oncogenes in the Immortalization of Neural Precursors", *Journal of Neuroscience Research,* 24:9–20 (1989).

Murphy, M., et al., "Cell Lines Derived from Mouse Neural Crest are Representative of Cells at Various Stages of Differentiation", *Journal of Neurobiology,* 22(5):522–535 (1991).

Shah, N. M., et al., "Glial Growth Factor Restricts Mammalian Neural Crest Stem Cells to a Glial Fate", *No. 005 Article,* 11 pp (1994).

Stemple, D. L., et al., "Isolation of a Stem Cell for Neurons and Glia from the Mammalian Neural Crest", *Cell,* 71:973–985 (1992).

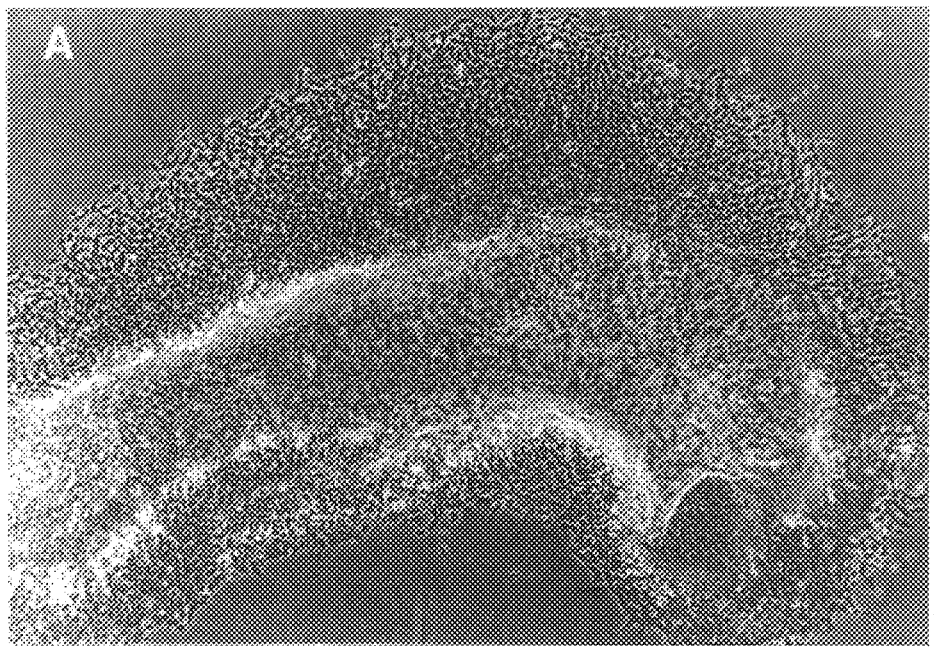
FIG._1A
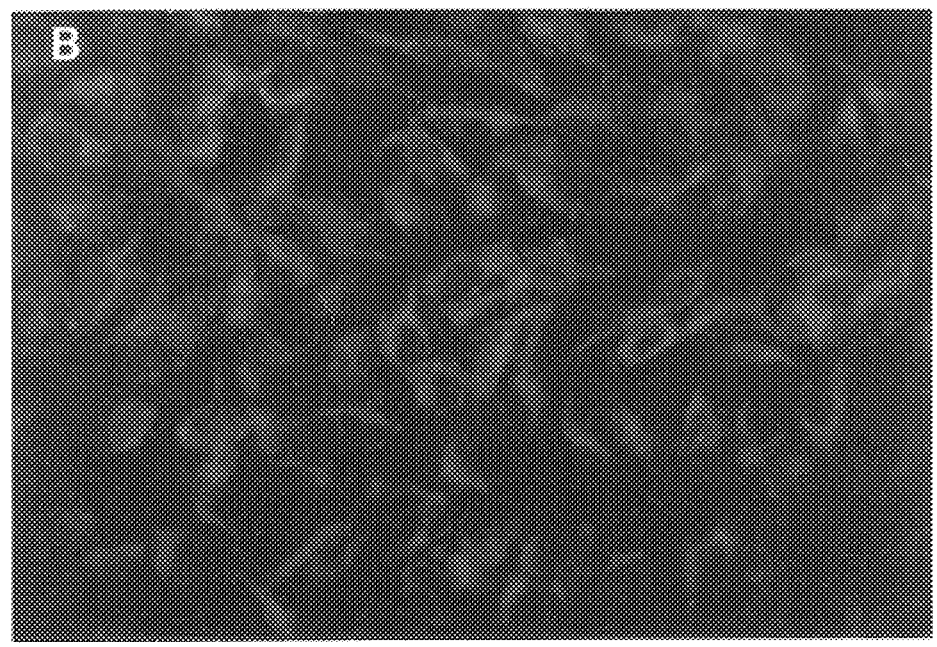
FIG._1B

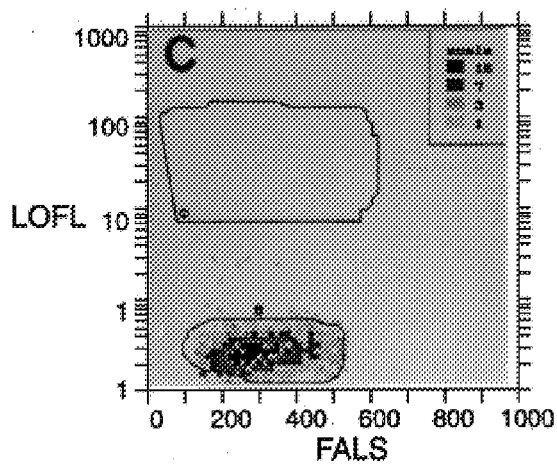
FIG._1C
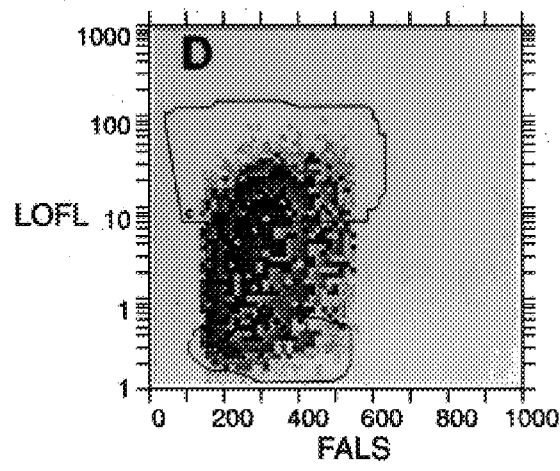
FIG._1D

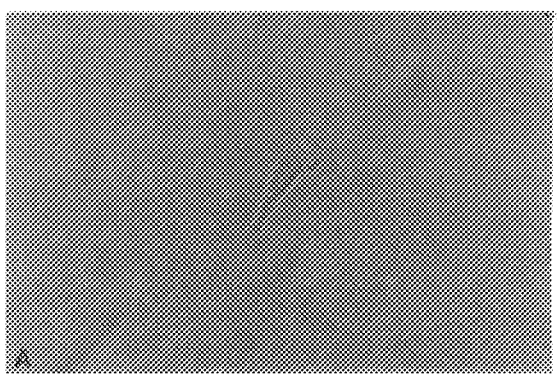
FIG._2A
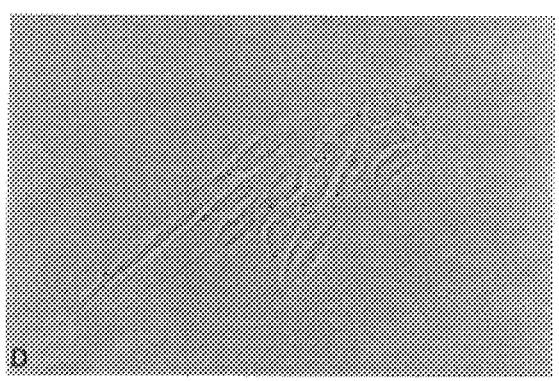
FIG._2D
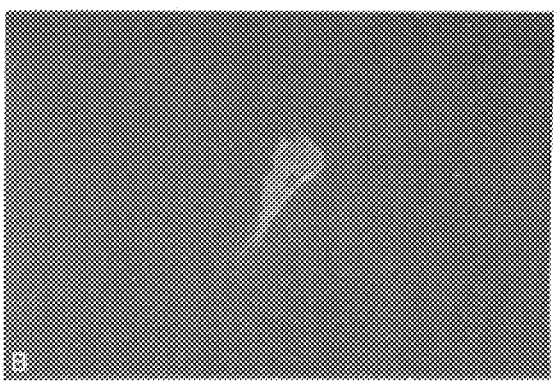
FIG._2B
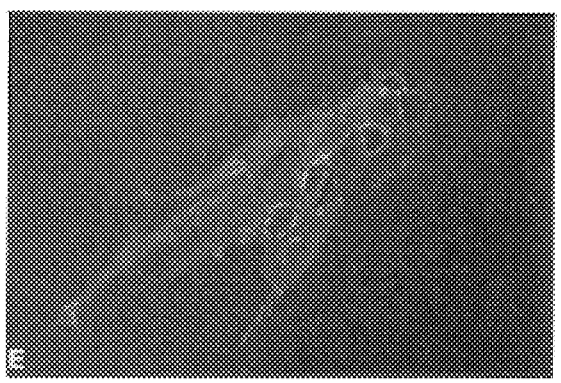
FIG._2E
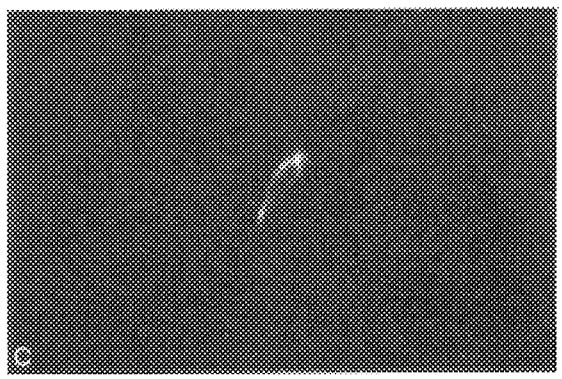
FIG._2C
FIG._2F

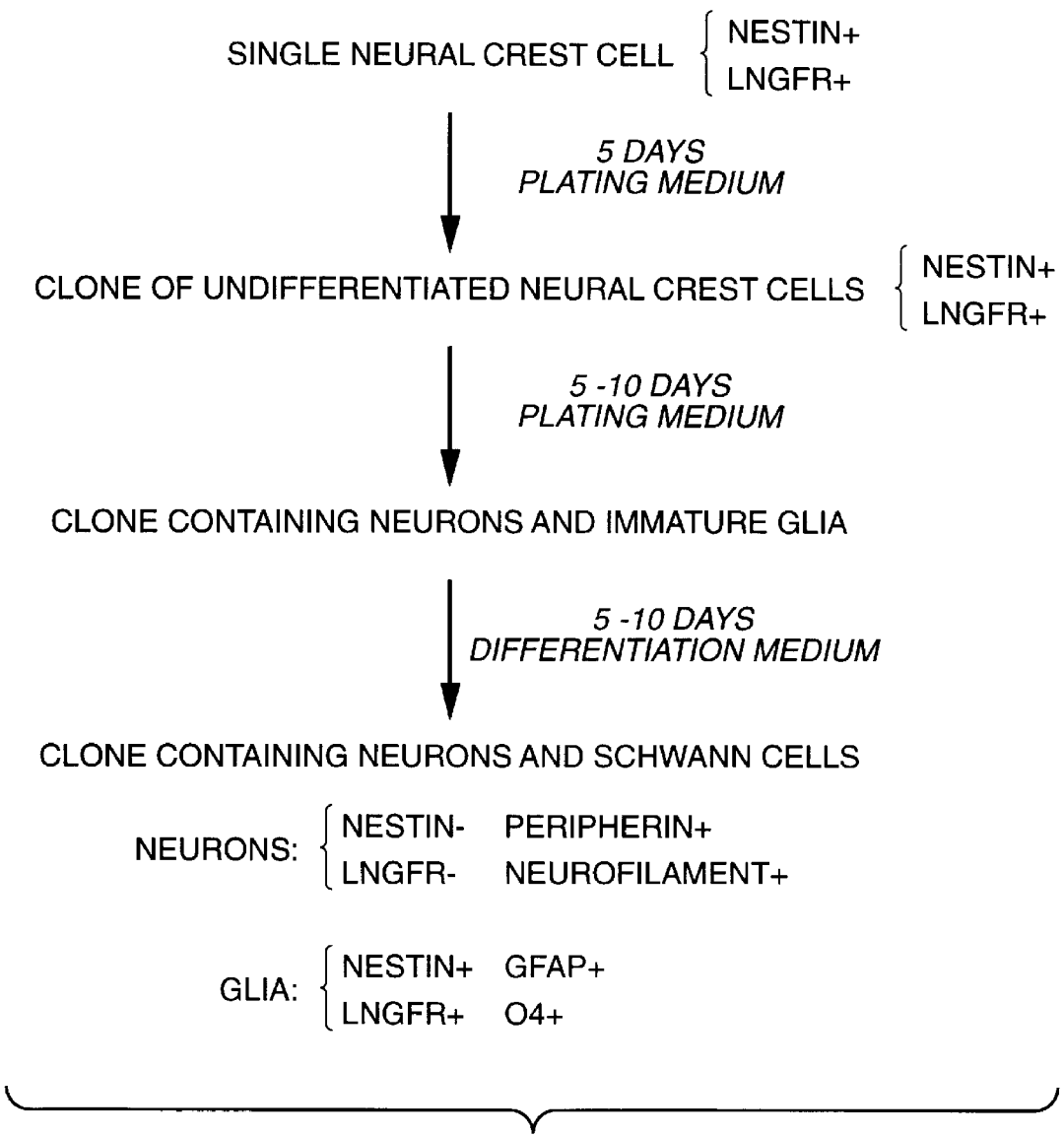
FIG._3

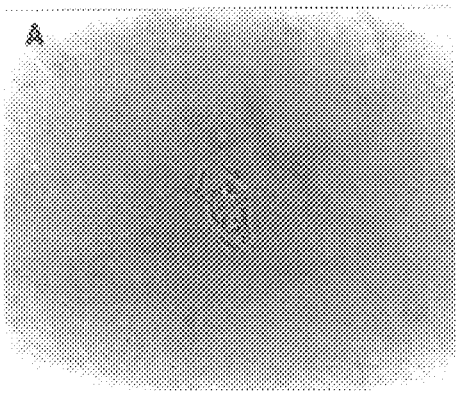
FIG._4A
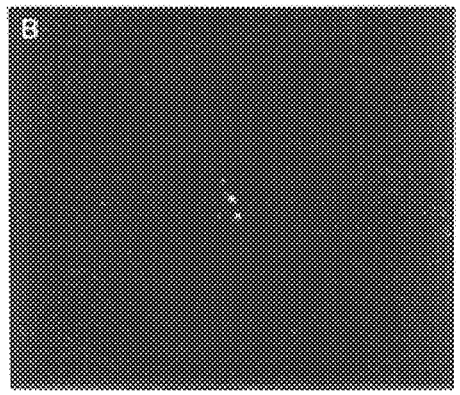
FIG._4B
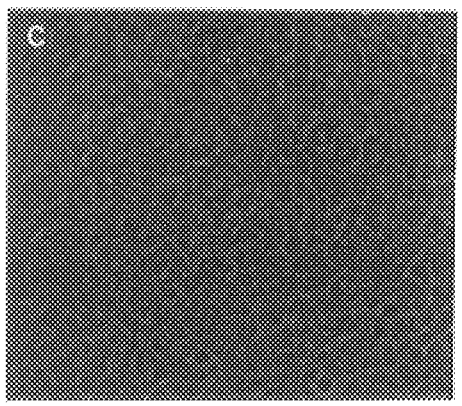
FIG._4C
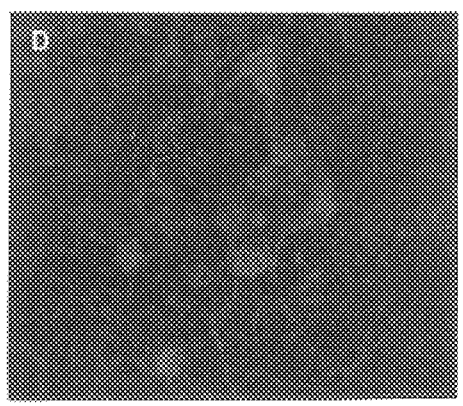
FIG._4D
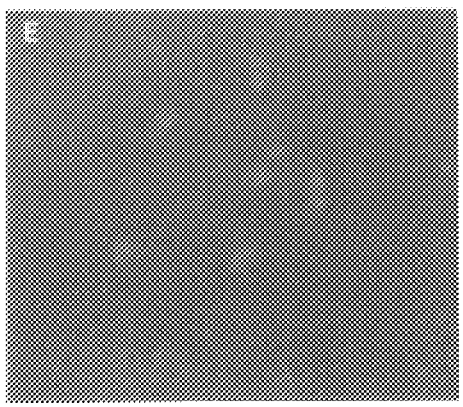
FIG._4E
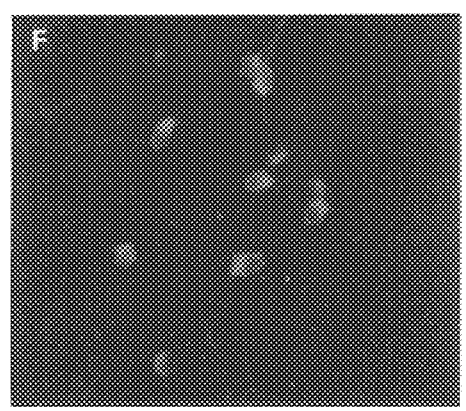
FIG._4F

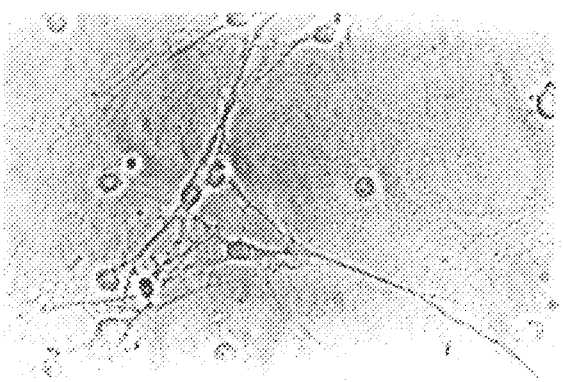
FIG._5A
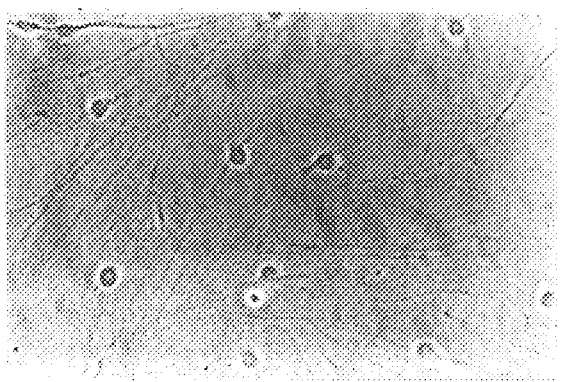
FIG._5D
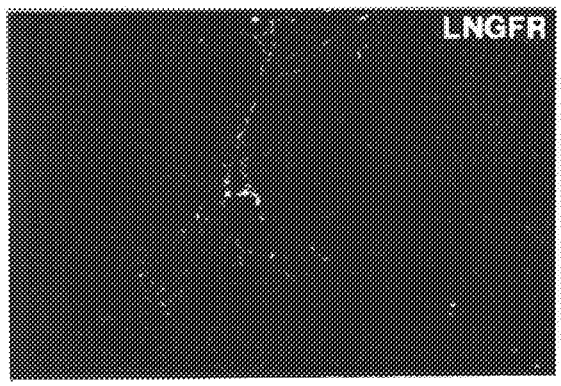
FIG._5B
FIG._5E
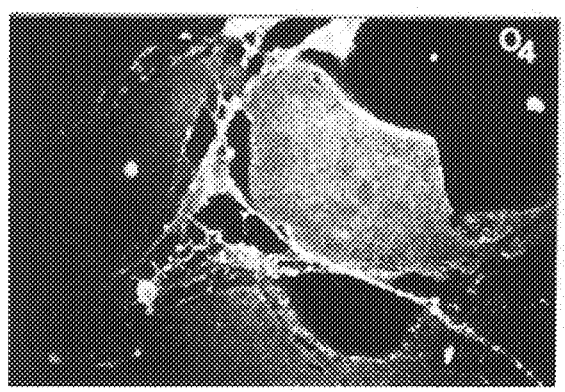
FIG._5C
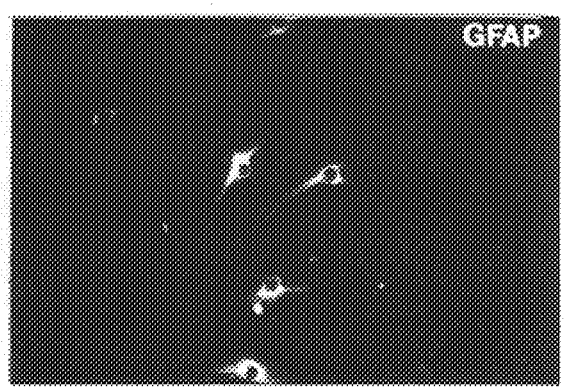
FIG._5F

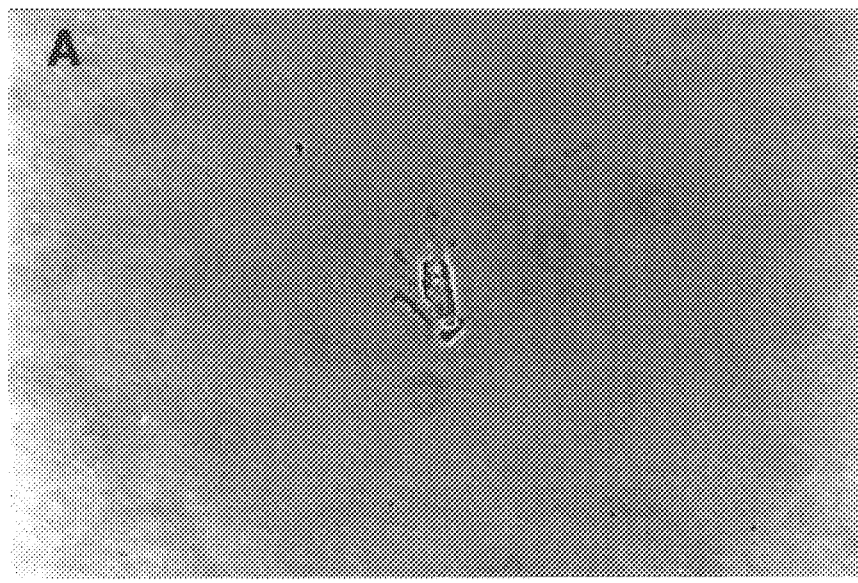
FIG._6A
FIG._6B

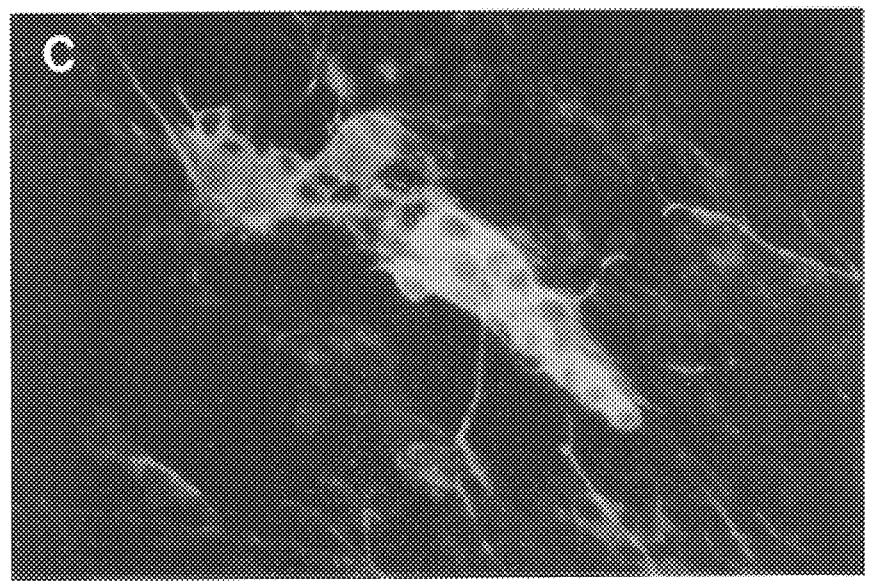
FIG._6C
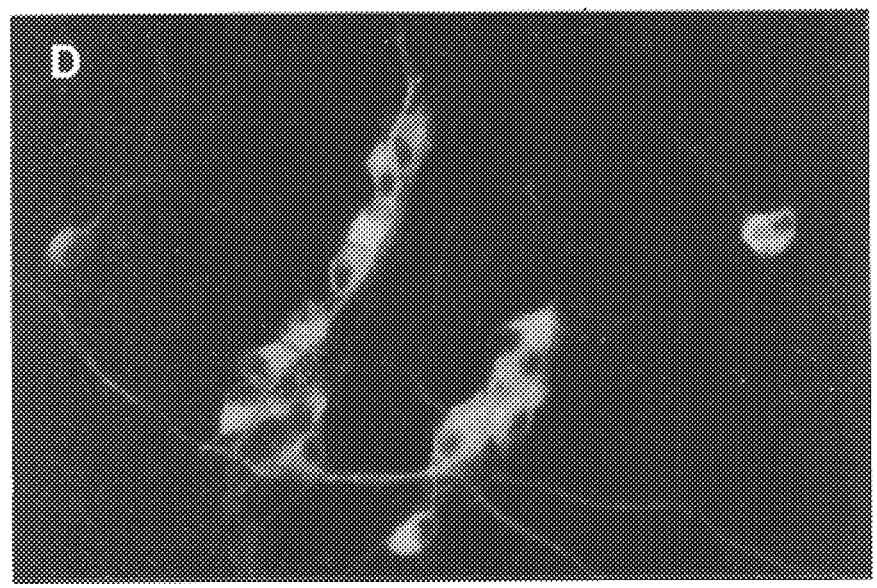
FIG._6D

SELF-RENEWAL OF MAMMALIAN NEURAL CREST CELLS

SINGLE NEURAL CREST FOUNDER CELL

↓ *5 -7 DAYS PLATING MEDIUM*

CLONE OF UNDIFFERENTIATED NEURAL CREST CELLS

↙ ↓ ↘

RECLONE AND IDENTIFY SECONDARY FOUNDER CELLS

↓ ↓ ↓ *10 DAYS DIFFERENTIATION MEDIUM*

SCORE CLONES AS MIXED, GLIAL OR OTHER

↓ ↓ ↓ *10 DAYS DIFFERENTIATION MEDIUM*

FIX AND STAIN FOR ANTIGENIC MARKERS

*FIG._7*

1° CLONE (DAY 7)
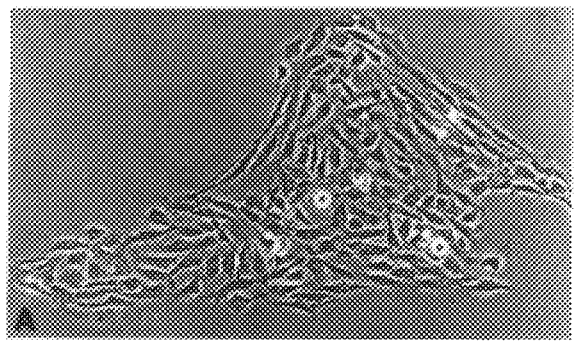
FIG._8A
2° FOUNDERS
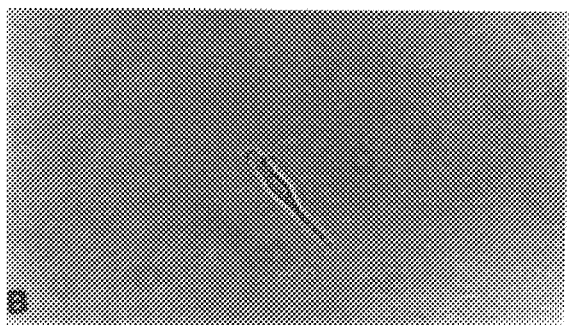
FIG._8B
2° FOUNDERS
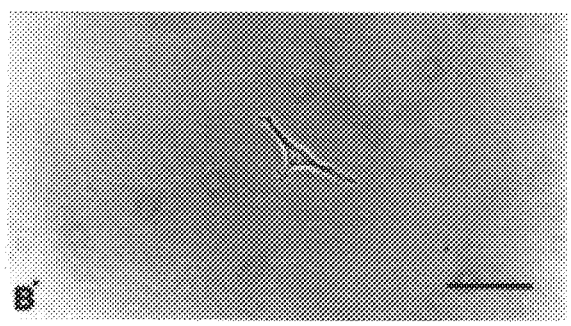
FIG._8B'
2° CLONES (DAY 17)
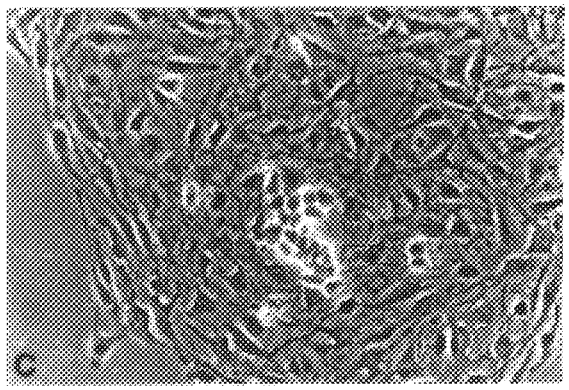
FIG._8C
2° CLONES (DAY 17)
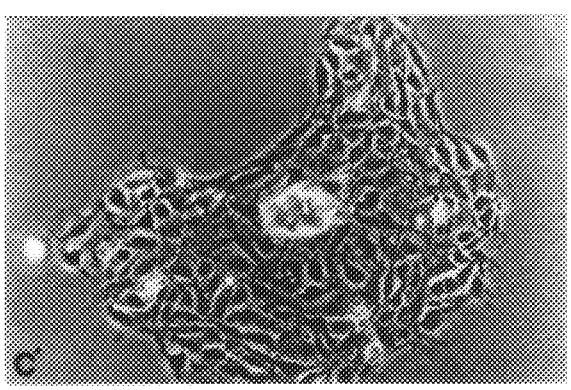
FIG._8C'

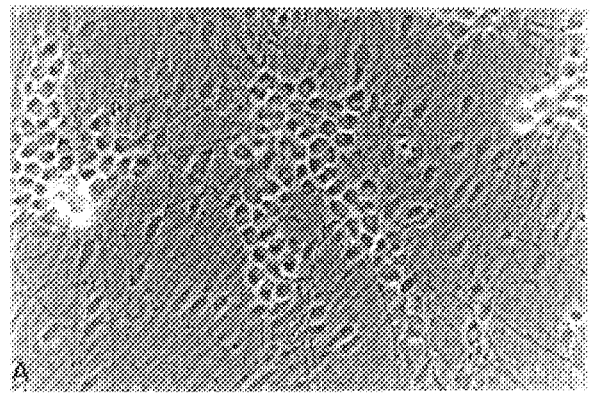
*FIG._9A*
NF160
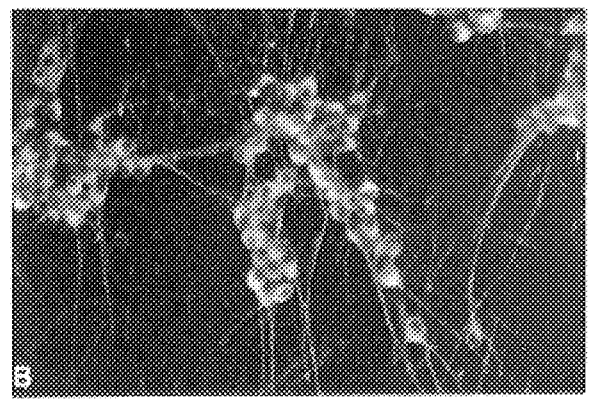
*FIG._9B*
GFAP
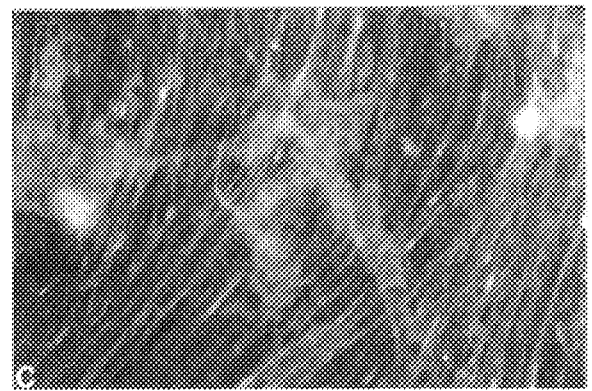
*FIG._9C*

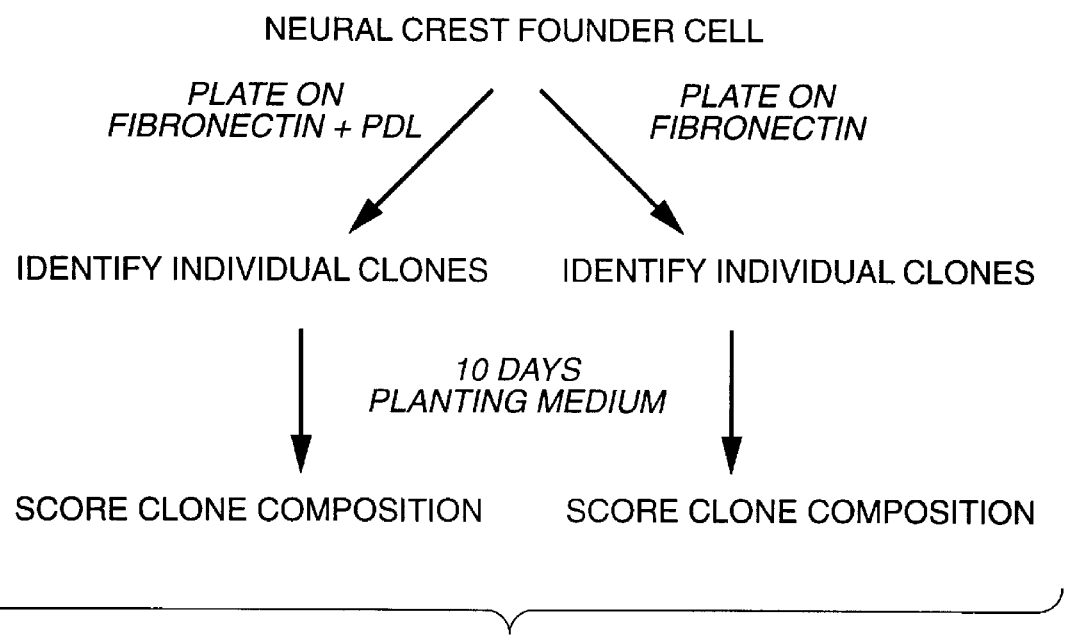
FIG._10

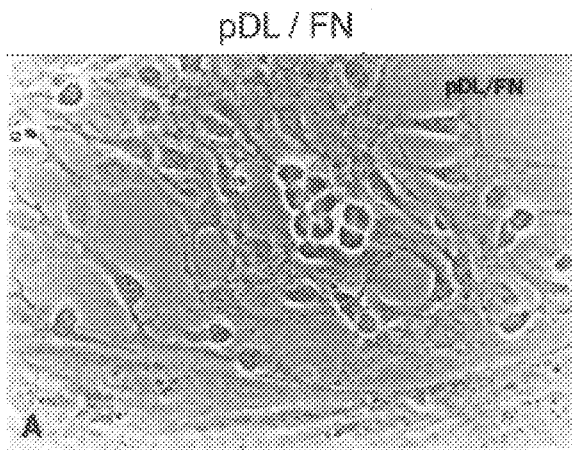
FIG._11A
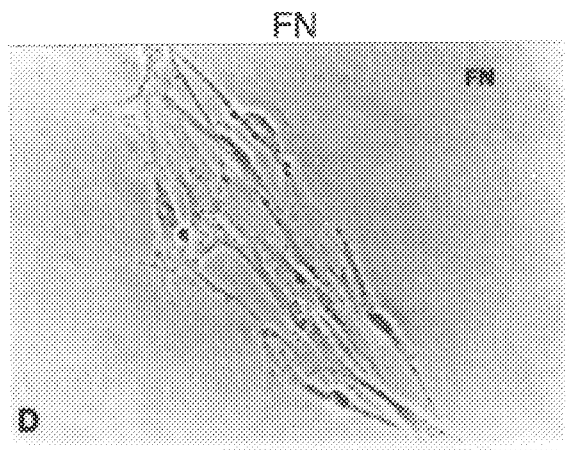
FIG._11D
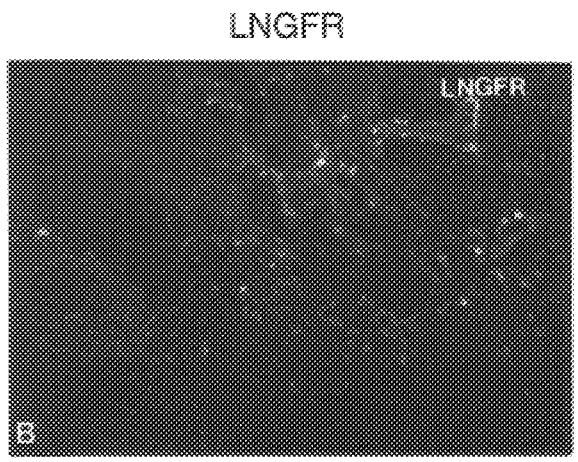
FIG._11B
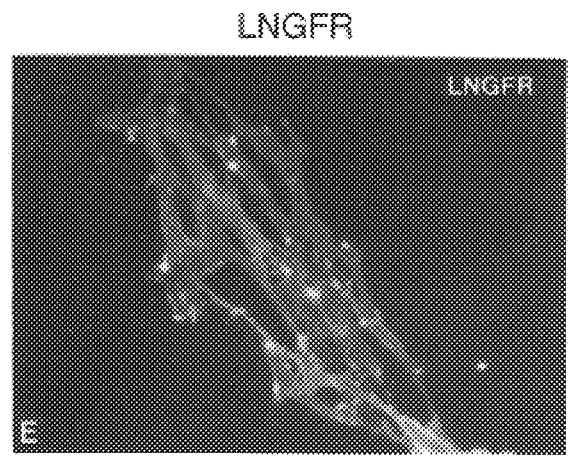
FIG._11E
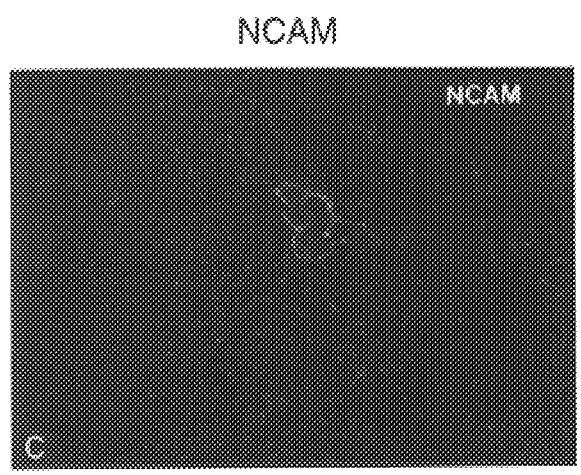
FIG._11C
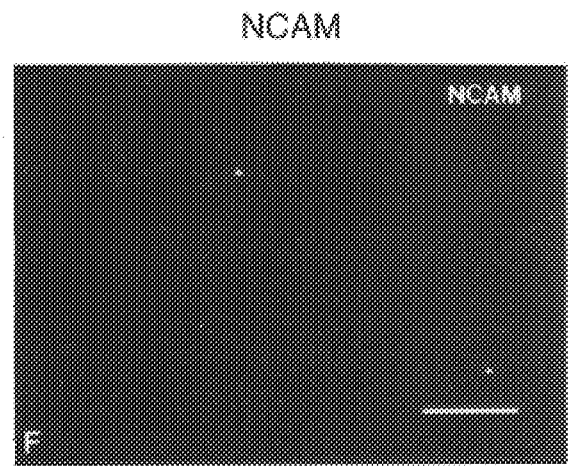
FIG._11F

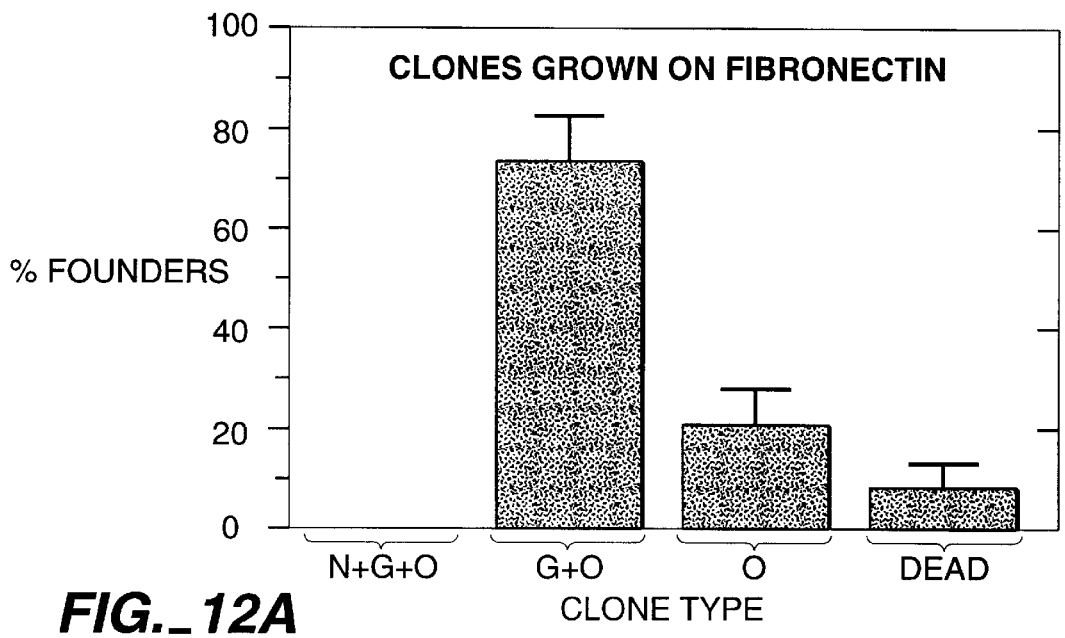
FIG._12A
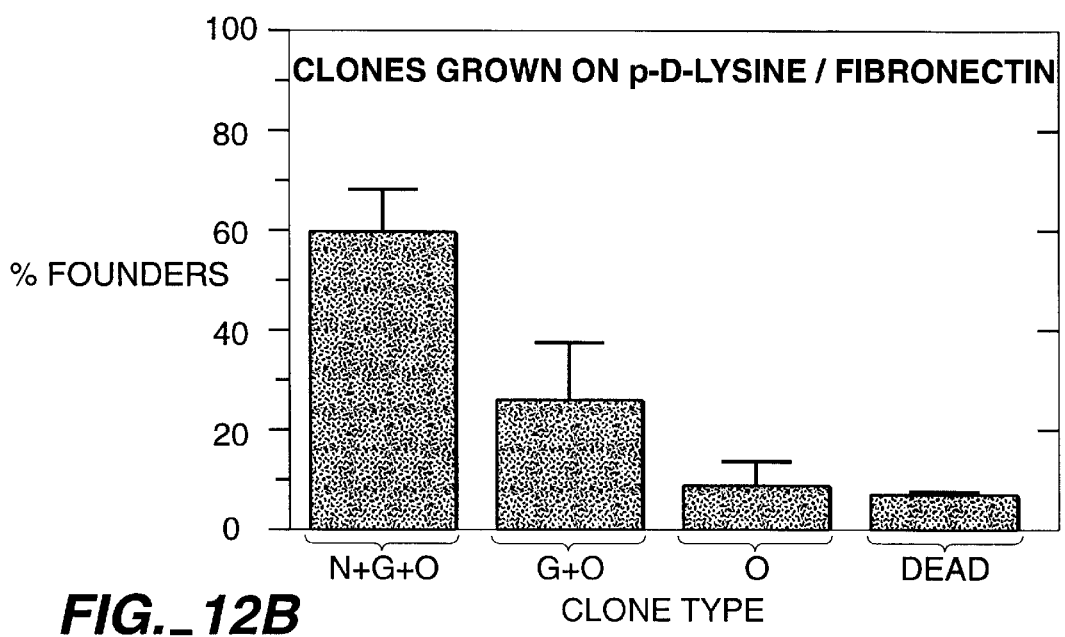
FIG._12B

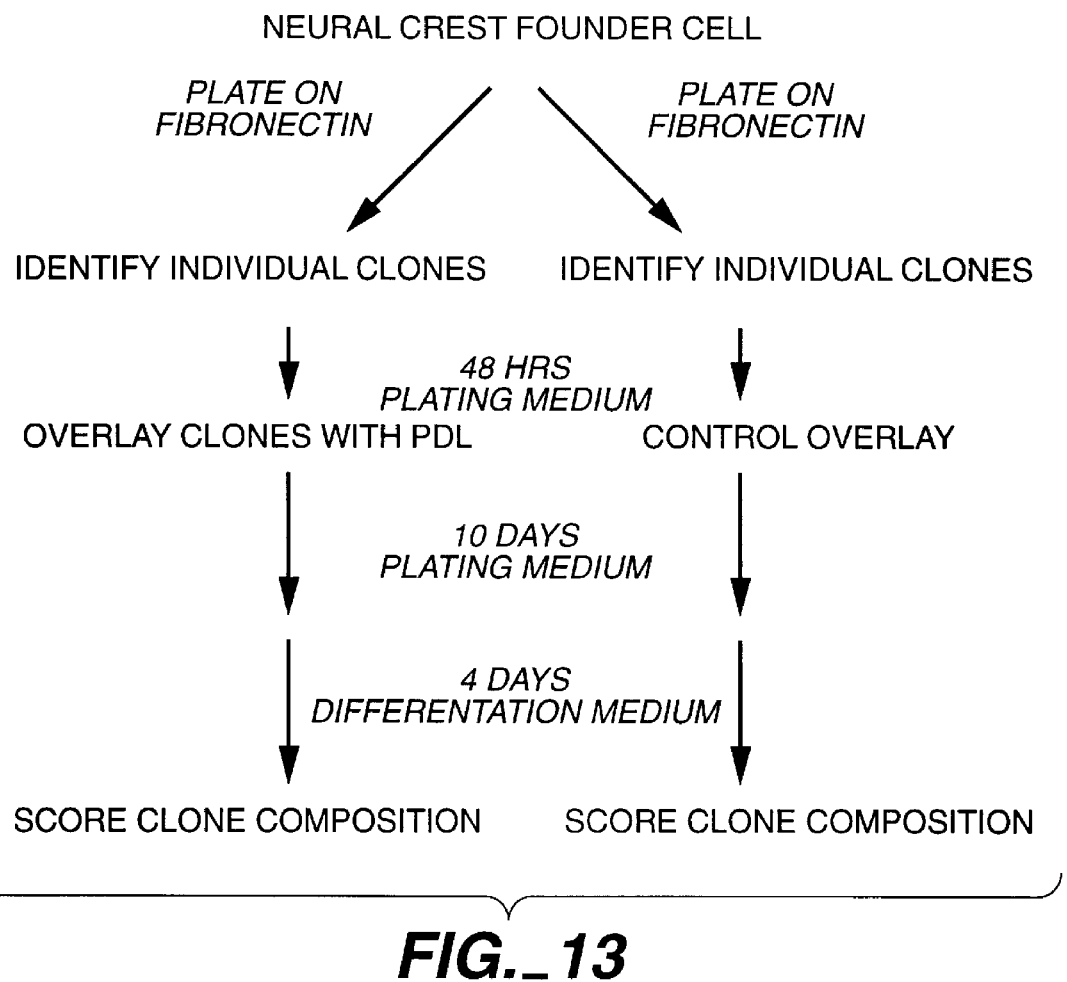
FIG._13

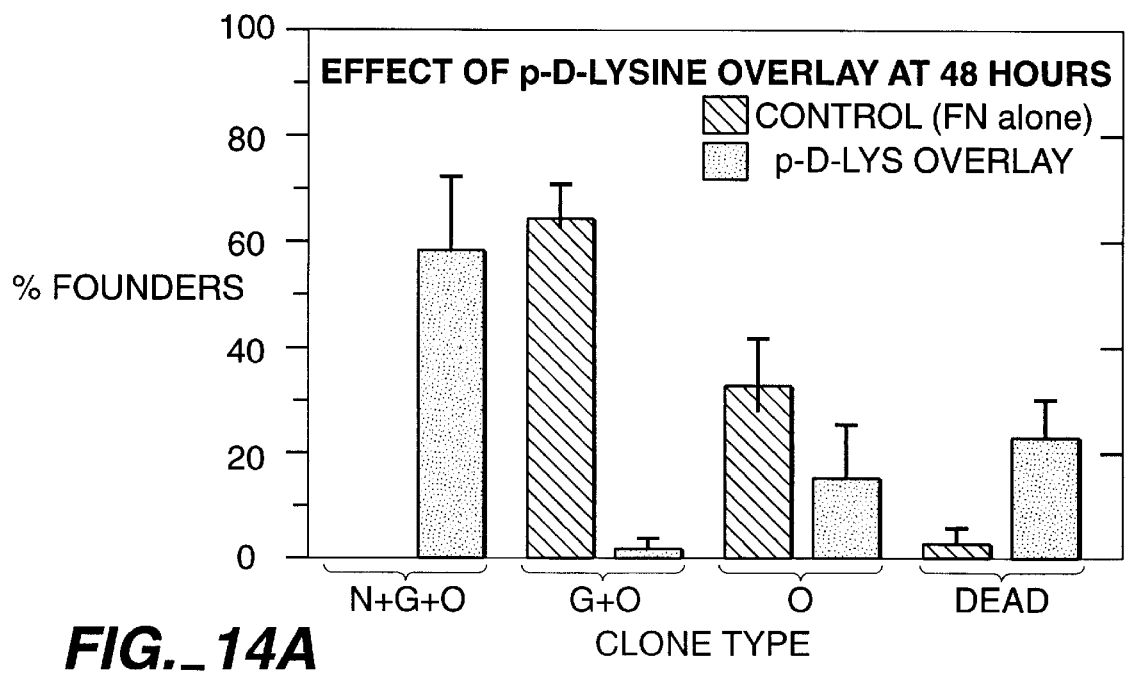
FIG._14A
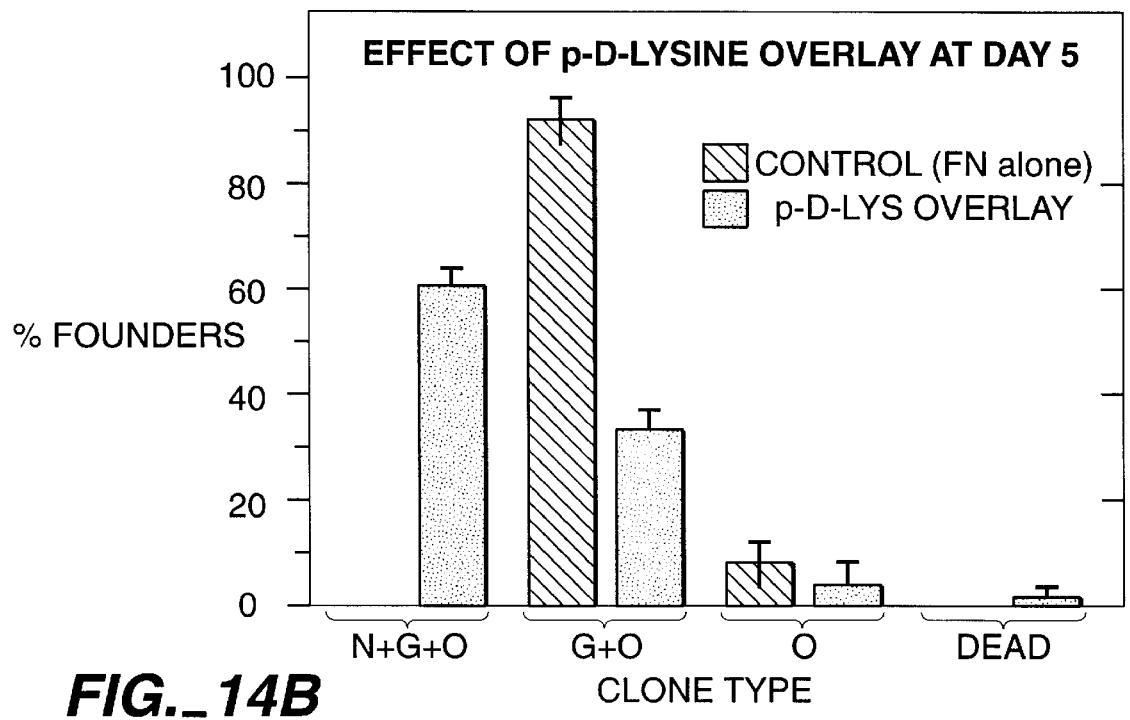
FIG._14B

IN VITRO METHOD FOR OBTAINING AN ISOLATED POPULATION OF MAMMALIAN NEURAL CREST STEM CELLS

This is a continuation of application Ser. No. 07/969,088 filed Oct. 29, 1992, now abandoned which is a continuation-in-part of application Ser. No. 07/920,617 filed Jul. 27, 1992, now abandoned.

FIELD OF THE INVENTION

The invention relates to the isolation, regeneration and use of mammalian multipotent neural stem cells and progeny thereof.

BACKGROUND

The neural crest is a transient embryonic precursor population, whose derivatives include cells having widely different morphologies, characteristics and functions. These derivatives include the neurons and glia of the entire peripheral nervous system, melanocytes, cartilage and connective tissue of the head and neck, stroma of various secretory glands and cells in the outflow tract of the heart (for review, see Anderson, D. J. 1989. Neuron, 3, 1–12). Much of the knowledge of the developmental potential and fate of neural crest cells comes from studies in avian systems. Fate maps have been established in aves and provide evidence that several different crest cell derivatives may originate from the same position along the neural tube (Le Dourain, N. M., 1980, Nature 286, 663–669). Schwann cells, melanocytes and sensory and sympathetic neurons can all derive from the truncal region of the neural tube. On the other hand, some derivatives were found to originate from specific regions of the crest, e.g., enteric ganglia from the vagal and sacral regions. These studies also revealed that the developmental potential of the neural crest population at a given location along the neural tube is greater than its developmental fate. This suggests that the new environment encountered by the migrating crest cells influences their developmental fate.

Single-cell lineage analysis in vivo, as well as clonal analysis in vitro, have reportedly shown that early avain neural crest cells are multipotential during, or shortly after, their detachment and migration from the neural tube. In avian systems, certain clones derived from single neural crest cells in culture were reported to contain both catecholaminergic and pigmented cells (Sieber-Blum, M. and Cohen, A. M. 1980, Dev. Biol., 80, 96–106). Baroffio, A. et al. (1988, Proc. Natl. Acad. Sci. USA, 85, 5325–5329) reported that avian neural crest cells from the cephalic region could generate clones which gave rise to highly heterogeneous progeny when grown on growth-arrested fibroblast feeder cell layers.

In vivo demonstration of the multipotency of early neural crest cells was reported in chickens by Bronner-Fraser, M. and Fraser, S., 1989, Neuron, 3, 755–766. Individual neural crest cells, prior to their migration from the neural tube, were injected with a fluorescent dye. After 48 hours, the clonal progeny of injected cells were found to reside in many or all of the locations to which neural crest cells migrate, including sensory and sympathetic ganglia, peripheral motor nerves and the skin. Phenotypic analysis of the labelled cells revealed that at least some neural crest cells are multipotent in vivo.

Following migration from the neural tube, these early multipotent crest cells become segregated into different sublineages, which generate restricted subsets of differentiated derivatives. The mechanisms whereby neural crest cells become restricted to the various sublineages are poorly understood. The fate of neural crest derivatives is known to be controlled in some way by the embryonic location in which their precursors come to reside (Le Douarin, N. M., 1982, The Neural Crest., Cambridge University Press, Cambridge, UK). The mechanism of specification for neural crest cells derivatives is not known. In culture studies described above, investigators reported that clones derived from primary neural crest cells exhibited a mixture of phenotypes (Sieber-Blum, M. and Cohen, A. M. 1980, ibid; Baroffio, A. et al., 1988, ibid; Cohen, A. M. and Konigsberg, I. R.,1975, Dev. Biol., 46, 262–280; Dupin, E. et al., 1990, Proc. Natl. Acad. Sci. USA, 87, 1119–1123). Some clones contained only one differentiated cell type whereas other clones contained many or all of the assayable crest phenotypes.

The observation that apparently committed progenitors and multipotent cells coexist in the neural crest may be interpreted to reflect a pre-existing heterogeneity in the population of primary crest cells or it may reflect asynchrony in a population of cells that undergoes a progressive restriction in developmental potential. Given the uncertainty in the art concerning the developmental potential of neural crest cells, it is apparent that a need exists for the isolation of neural crest cells in clonal cultures. Although culture systems have been established which allow the growth and differentiation of isolated avian neural crest cells thereby permitting phenotypic identification of their progeny, culture conditions which allow the self-renewal of multipotent mammalian neural crest cells have not been reported. Such culture conditions are essential for the isolation of mammalian neural crest stem cells. Such stem cells are necessary in order to understand how multipotent neural crest cells become restricted to the various neural crest derivatives. In particular, culture conditions which allow the growth and self-renewal of mammalian neural crest stem cells are desirable so that the particulars of the development of these mammalian stem cells may be ascertained. This is desirable because a number of tumors of neural crest derivatives exist in mammals, particularly humans. Knowledge of mammalian neural crest stem cell development is therefore needed to understand these disorders in humans. Additionally, the ability to isolate and grow mammalian neural crest stem cells in vitro allows for the possibility of using said stem cells to treat peripheral neurological disorders in mammals, particularly humans.

Accordingly, it is an object herein to provide clonal cultures of mammalian neural crest stem cells and their progeny in feeder cell-independent cultures. An object of the invention is directed to the demonstration that multipotential stem cells exist in the neural crest. Another object of the invention is the demonstration that these neural crest stem cells have at least limited self regeneration capacity and undergo lineage restriction in a manner that is sensitive to the local environment. A further object of the invention is to provide methods which allow the growth and regeneration of neural crest stem cells in feeder cell-independent cultures. Another object of the invention is to provide methods which allow the differentiation of these neural crest stem cells into at least the progenitors for, as well as, more differentiated neurons and glia of the peripheral nervous system (PNS). A further object of the invention is to provide methods which allow for the identification of mammalian neural crest stem cells using transplantation assays. Still further, an object of the invention is to provide methods for transplanting neural crest stem cells or their progeny into a mammal.

A further object of the invention is to extend the methods used to provide clonal cultures of mammalian neural crest stem cells and their progeny to the detection or purification of glial or neuronal progenitor cells or multipotent stem cell precursors of such cells from tissues other than the embryonic neuronal crest and to provide methods which allow the growth, regeneration and differentiation of such cells. Still further, it is an object herein to provide methods for transplanting progenitors of such glial and neuronal cells and multipotent stem cell precursor thereof into a mammal.

SUMMARY OF THE INVENTION

In accordance with the forgoing objects, the invention includes methods for the isolation and clonal propagation of mammalian neural crest stem cells. The methods employ novel separation and culturing regimens and bioassays for establishing the generation of neural crest stem cell derivatives. These methods result in the production of non-transformed neural crest stem cells and their progeny. The invention demonstrates, at the clonal level, the self regeneration and asymmetrical division of mammalian neural crest stem cells for the first time in feeder cell-independent cultures. Lineage restriction is demonstrated within a developing clone and is shown to be sensitive to the local environment. Neural crest stem cells cultured on a mixed substrate of poly-D-lysine and fibronectin generate PNS neurons and glia, but on fibronectin alone the stem cells generate PNS glia but not neurons. The neurogenic potential of the stem cells, while not expressed, is maintained over time on fibronectin. Therefore, both the overt differentiation and maintenance of a latent developmental potential of neural crest stem cells are shown to be sensitive to the environment. The invention further includes transplantation assays which allow for the identification of mammalian neural crest stem cells from various tissues. It also includes methods for transplanting mammalian neural crest stem cells and/or neural or glial progenitors into mammals.

The invention also includes methods for obtaining a cellular compositions from mammalian tissue comprising one or more cells having at least one property characteristic of a glial or neural progenitor cell or a multipotent stem cell precursor of such cells. The method comprises preparing a suspension comprising a population of cells from a mammalian tissue; contacting the cell suspension with a culture medium and substrate which permits self-renewal of one or more of the glial or neural progenitor cells or multipotent stem cell precursor, if present, in the cell suspension; and identifying one or more such cells by its ability to self-renew and differentiate Feeder-cell independent culture.

The invention also includes alternate methods for obtaining a cellular composition comprising one or more cells having at least one property characteristic of a glial or neural progenitor cells or a multipotent stem cell precursor thereof. The method comprises preparing a suspension comprising cells from a mammalian tissue; contacting the suspension with an antibody capable of forming a complex with a neural cell-specific surface marker on said glial or neural progenitor cells or multipotent stem cell precursor; and isolating the complex, if formed, to obtain said cellular composition.

The invention also includes cells made according to any of the foregoing methods.

Still further, the invention includes methods for immortalizing such cell lines by transforming a glial or neural progenitor cell or multipotent stem cell precursor thereof with a vector comprising an immortalizing oncogene or virus.

BRIEF DESCRIPTION OF THE DRAWINGS

FIG. 1A depicts the migration of rat neural crest cells from the neural tube.

FIG. 1B demonstrates the expression of LNGFR and nestin by neural crest cells.

FIGS. 1C and 1D show the FACS profile from neural crest cells stained with anti-LNGFR (1D) and a control showing the background staining of the secondary antibody (1C).

FIGS. 2(A–F) demonstrate the clonal expansion of $LNGFR^+$, $nestin^+$ rat neural crest cells.

FIG. 3 is a flow chart summarizing experiments demonstrating the multipotency of mammalian neural crest cells.

FIGS. 4(A–F) demonstrate the expression of neuronal traits in clones derived from $LNGFr^+$ founder cells.

FIGS. 5(A–F) demonstrate the expression of Schwann cell phenotype by neural crest-derived glia.

FIGS. 6(A–D) shows the expression of peripherin, GFAP, and $O_4$ in a clone derived from a $LNGFR^+$ founder cell.

FIG. 7 is a flow chart summarizing experiments demonstrating the self-renewal of mammalian neural crest cells.

FIGS. 8(A, B, B', C and C') demonstrates the self-renewal of multipotent neural crest cells.

FIGS. 9(A–C) demonstrate the multipotency of secondary founder cells.

FIG. 10 provides a flow chart summarizing experiments demonstrating the substrate effect on the fate of mammalian neural crest cells.

FIGS. 11(A–F) demonstrate that the neuronal differentiation of multipotent neural crest cells is affected by their substrate.

FIGS. 12(A and B) summarize the percentage of different clone types which result when founder cells are grown on either FN or FN/PDL substrates.

FIG. 13 provides a flow chart summarizing experiments demonstrating the instructive effect of the substrate on neural crest cell fate.

FIGS. 14(A and B) summarize the percentage of the different clone types which result when founder cells are treated with a PDL lysine overlay at 48 hours (panel A) or day 5 (panel B).

DETAILED DESCRIPTION OF THE INVENTION

The invention is directed, in part, to the isolation and clonal propagation of non-transformed mammalian neural crest stem cells and to multipotent neural stem cells from other embryonic and adult tissue. The invention also includes the production of neural crest stem cell and multipotent neural stem cell derivatives including progenitor and more differentiated cells of the neuronal and glial lineages. The invention is illustrated using neural crest stem cells isolated from the rat. The invention, however, encompasses all mammalian neural crest stem cells and multipotent neural stem cells and their derivatives and is not limited to neural crest stem cells from the rat. Mammalian neural crest stem cells and multipotent neural stem cells and their progeny can be isolated from tissues from human and non-human primates, equines, canines, felines, bovines, porcines, lagomorphs, etc.

As used herein, the term "non-transformed cells" means cells which are able to grow in vitro without the need to immortalize the cells by introduction of a virus or portions of a viral genome containing an oncogene(s) which confers altered growth properties upon the cells by virtue of the expression of viral genes within the transformed cells. These viral genes typically have been introduced into cells by means of viral infection or by means of transfection with DNA vectors containing isolated viral genes.

As used herein, the term "feeder-cell independent culture" or grammatical equivalents means the growth of cells in vitro in the absence of a layer of different cells which generally are first plated upon a culture dish to which cells from the tissue of interest are added. The "feeder" cells provide a substratum for the attachment of the cells from the tissue of interest and additionally serve as a source of mitogens and survival factors. The feeder-cell independent cultures herein utilize a chemically defined substratum, for example fibronectin (FN) or poly-D-lysine (PDL) and mitogens or survival factors are provided by supplementation of the liquid culture medium with either purified factors or crude extracts from other cells or tissues. Therefore, in feeder-cell independent cultures, the cells in the culture dish are primarily cells derived from the tissue of interest and do not contain other cell types required to support the growth of the cells derived from the tissue of interest.

As used herein, the term "clonal density" means a density sufficiently low enough to result in the isolation of single, non-impinging cells when plated in a culture dish, generally about 225 cells/100 mm culture dish.

As used herein, the term "neural crest stem cell" means a cell derived from the neural crest which is characterized by having the properties (1) of self-renewal and (2) asymmetrical division; that is, one cell divides to produce two different daughter cells with one being self (renewal) and the other being a cell having a more restricted developmental potential, as compared to the parental neural crest stem cell. The foregoing however is not to be construed to mean that each cell division of a neural crest stem cell gives rise to an asymmetrical division. It is possible that a division of a neural crest stem cell can result only in self-renewal, in the production of more developmentally restricted progeny only, or in the production of a self-renewed stem cell and a cell having restricted developmental potential.

As used herein, the term "multipotent neural stem cell" refers to a cell having properties similar to that of a neural crest stem cell but which is not necessarily derived from the neural crest. Rather, as described hereinafter, such multipotent neural stem cells can be derived from various other tissues including neural epithelial tissue from the brain and/or spinal cord of the adult or embryonic central nervous system or neural epithelial tissue which may be present in tissues comprising the peripheral nervous system. In addition, such multipotent neural stem cells may be derived from other tissues such as lung, bone and the like utilizing the methods disclosed herein. It is to be understood that such cells are not limited to multipotent cells but may comprise a pluripotent cell capable of regeneration and differentiation to different types of neurons and glia, e.g., PNS and CNS neurons and glia or progenitors thereof. In this regard, it should be noted that the neural crest stem cells described herein are at least multipotent in that they are capable, under the conditions described, of self-regeneration and differentiation to some but not all types of neurons and glia in vitro. Thus, a neural crest stem cell is a multipotent neural stem cell derived from a specific tissue, i.e., the embryonic neural tube.

In most embodiments, neural crest stem cells are further characterized by a neural cell-specific surface marker. Such surface markers in addition to being found on neural chest stem cells may also be found on other multipotent neural stems derived therefrom, e.g., glial and neuronal progenitor cells of the peripheral nervous system (PNS) and central nervous system (CNS). An example is the cell surface expression of a nerve growth factor receptor on neural crest stem cells. In rat, humans and monkeys this nerve growth factor receptor is the low-affinity nerve growth factor receptor (LNGFR). Such stem cells may also be characterized by the expression of nestin, an intracellular intermediate filament protein. Neural crest stem cells may be further characterized by the absence of markers associated with mature PNS neuronal or glial cells. In the rat such markers include sulfatide, glial fibrillary acidic protein (GFAP) and myelin protein $P_o$ in PNS glial cells and peripherin and neurofilament in PNS neuronal cells.

LNGFR is a receptor for nerve growth factor, a neurotrophic factor shown to be responsible for neuronal survival in vivo. LNGFR is found on several mammalian cell types including neural crest cells and Schwann cells (glial cells of the PNS) as well as on the surface of cells in the ventricular zone throughout the embryonic central nervous systems. (See, e.g., Yan and Johnson (1988) *J. Neurosci* 8, 3481–3496 and Heuer, J. G, et al., (1980) *Neuron* 5, 283–296 which studied such cells in the rat and chick systems, respectively.) Antibodies specific for LNGFR have been identified for LNGFR from rat [monoclonal antibodies 217c (Peng, W. W. et al., 1982, *Science,* 215, 1102–1104) and 192-Ig (Brockes, J. P. et al, 1977, *Nature,* 266, 364–366 and Chandler, C. E. et al, 1984, *J. Biol. Chem.,* 259, 6882–6889] and human (Ross, A. H. et al., 1984, *Proc. Natl. Acad. Sci. USA,* 81, 6681–6685; Johnson, et al., (1986) *Cell* 47, 545–554; Loy, et al., (1990) *J. Neurosci Res.* 27, 651–644). The monoclonal antibody against human LNGFR has been reported to cross-react with LNGFR from monkeys (Mufson, E. G. et al., 1991, *J. Comp. Neurol.,* 308, 555–575). The DNA sequence has been determined for rat and human LNGFR (Radeke, M. J. et al., 1987, *Nature,* 325, 593–597 and Chao, M. V. et al., 1986, *Science,* 232, 518–521, respectively) and is highly conserved between rat and human. Using standard techniques, it is possible to generate monoclonal antibodies specific for LNGFR from any desired mammalian species by first isolating the nucleic acid encoding the LNGFR protein. One protocol for obtaining such nucleic acid sequences uses one or more nucleic acid sequences from a region of the LNGFR gene which is highly conserved between mammalian species, e.g., rat and human, as a hybridization probe to screen a cDNA library derived from mammalian tissue from the desired species (Sambrook, J., Fritsch, E. F., and Maniatis, T. 1989. Cold Spring Harbour Laboratory Press. *Molecular Cloning: A Laboratory Manual,* 2nd Ed., pp. 8.3–8.80, 9.47–9.58 and 11.45–11.55.). The cDNA sequences are then used to express the LNGFR protein in an expression host from which the LNGFR protein is purified. Purification is performed using standard techniques such as chromatography on gel filtration, ion exchange or affinity resins. The purified LNGFR is then used to immunize an appropriate animal (e.g., mouse, rat, rabbit, hamster) to produce polyclonal antisera and to provide spleen cells for the generation of hybridoma cell lines secreting monoclonal antibodies specific for LNGFR of the desired species (Harlow, E. and Lane, D. 1988. Cold Spring Harbour Laboratory Press. *Antibodies: A Laboratory Manual.* pp. 139–242.).

Alternatively, the conserved nucleic acid sequences can be used to identify genomic clones encoding the LNGFR protein using standard techniques.

It is not always necessary to generate polyclonal or monoclonal antibodies that are species specific. Monoclonal antibodies against an antigenic determinant from one species may react against that antigen from more than one species. For example, as stated above, the antibody directed against the human LNGFR molecule also recognizes LNGFR on monkey cells. When crossreactive antibodies are available, there is no need to generate antibodies which are species specific using the methods described above.

Nestin, a second marker in the neural crest stem cell, is an intermediate filament protein primarily located intracellularly, which has been shown to be present in CNS neuroepithelial cells and Schwann cells in the peripheral nervous system of rats (Friedman et al., *J. Comp. Neurol.* 295, 43–51 (1990)). Monoclonal antibodies specific for rat nestin have been isolated: Rat 401, (Hockfield, S. and McKay, R. D. G., 1985, *J. Neurosci.*, 5(12), 3310–3328). A polyclonal rabbit anti-nestin antisera has been reported which recognizes mouse nestin (Reynolds, D. A. and Weiss, S., 1992, *Science,* 255, 1707–1710). The DNA sequences encoding the rat nestin gene have been cloned (Lendahl, U. et al., 1990, *Cell,* 60, 585–595). These DNA sequences are used to isolate nestin clones from other mammalian species. These DNA sequences are then used to express the nestin protein and monoclonal antibodies directed against various mammalian nestins are generated as described above for LNGFR.

As used herein, the term "glial progenitor cell" refers to a cell which is intermediate between the fully differentiated glial cell and a precursor multipotent neural stem cell from which the fully differentiated glial cell develops. In general, such glial progenitor cells are derived according to the methods described herein for isolating such cells from various tissues including adult and embryonic CNS and PNS tissue as well as other tissues which may potentially contain such progenitors.

As used herein, the term "PNS glial progenitor cell" means a cell which has differentiated from a mammalian neural crest stem cell which is committed to the PNS glial lineage and is a dividing cell but does not yet express surface or intracellular markers found on more differentiated, non-dividing PNS glial cells. Such progenitor cells are preferably obtained from neural crest stem cells isolated from the embryonic neural crest which have undergone further differentiation. However, equivalent cells may be derived from other tissue. When PNS glial progenitor cells are placed in appropriate culture conditions they differentiate into PNS glia expressing the appropriate differentiation markers, for example, sulfatide and GFAP.

Sulfatide is a glycolipid molecule found on the surface of Schwann cells and oligodendricytes in rats, mice, chickens and humans. The expression of sulfatide on Schwann cells is dependent upon on either axonal contact or exposure to cyclic AMP or analogs thereof, such as forskolin (Mirsky, R. et al., 1990, *Development,* 109, 105–116). Monoclonal antibodies specific for sulaftide have been reported (Sommer, I. and Schachner, M., 1981, *Dev. Biol.,* 83, 311–327). GFAP is an intermediate filament protein specifically expressed by astrocytes and glial cells of the CNS and by Schwann cells, the glial cells of the PNS (Jessen, K. R. and Mirsky, R., 1984, *J. Neurocytology,* 13, 923–934 and Fields, K. L. and Yen, S.-H., 1989, *J. Neuroimmuno.,* 8, 311–330). Monoclonal antibodies specific for GFAP have been reported (Debus et al., 1983, *Differentiation,* 25, 193–203). Mouse and human GFAP genes have been cloned (Cowan, N. J. et al., 1985, *N.Y. Acad. Sci.,* 455, 575–582 and Bongcamrudlowss, D. et al., 1991, *Cancer Res.,* 51, 1553–1560, respectively). These DNA sequences are used to isolate GFAP clones from other mammalian species. These DNA sequences are then used to express the GFAP protein and monoclonal antibodies directed against various mammalian GFAPs are generated as described above for LNGFR.

As used herein, the term "factors permissive for PNS glial cell differentiation" means compounds, such as, but not limited to, protein or steroid molecules or substrates such as FN or PDL, which permit at least neural crest stem cells to become restricted to the PNS glial lineage. Such lineage-restricted progeny of neural crest stem cells include glial progenitor cells, which are at least bipotential, in that they can divide to give rise to self, as well as, more mature nondividing PNS glial cells.

As used herein, the term "neuronal progenitor cell" refers to a cell which is intermediate between the fully differentiated neuronal cell and a precursor multipotent neural stem cell from which the fully differentiated neuronal cell develops. In general, such neuronal progenitor cells are derived according to the methods described herein for isolating such cells from various tissues including adult and embryonic CNS and PNS tissue as well as other tissues which may potentially contain such progenitors.

As used herein, the term "PNS neuronal progenitor cell" means a cell which has differentiated from a mammalian neural crest stem cell which is committed to one or more PNS neuronal lineages and is a dividing cell but does not yet express surface or intracellular markers found on more differentiated, non-dividing PNS neuronal cells. Such progenitor cells are preferably obtained from neural crest stem cells isolated from the embryonic neural crest which have undergone further differentiation. However, equivalent cells may be derived from the tissue. When PNS neuronal progenitor cells are placed in appropriate culture conditions they differentiate into mature PNS neurons expressing the appropriate differentiation markers, for example, peripherin, neurofilament and high-polysialic acid neural cell adhesion molecule (high PSA-NCAM).

Peripherin, a 57 kDa intermediate filament protein, is expressed in adult rodents primarily in peripheral neurons. More limited expression of peripherin is found in some motoneurons of the spinal cord and brain stem and a limited group of CNS neurons. Peripherin is expressed in rat embryos primarily in neurons of peripheral ganglia and in a subset of ventral and lateral motoneurons in the spinal cord (Gorham, J. D. et al., 1990, *Dev. Brain Res.,* 57, 235–248). Antibodies specific for this marker have been identified in the rat (Portier, M. et al., 1983/84, *Dev. Neurosci.,* 6, 335–344). The DNA sequences encoding the rat peripherin gene have been cloned (Thompson, M. A. and Ziff, E. B., 1989, *Neuron,* 2, 1043–1053). These DNA sequences are used to isolated DNA sequences for the peripherin gene in other mammals that are used to express the protein and generate antibodies directed against other mammalian peripherin proteins, as described above for LNGFR.

Neurofliaments are neuron-specific intermediate filament proteins. Three neurofilament (NF) proteins have been reported: NF68, a 68 kD protein also called NF-L (Light); NF160, a 160 kD protein also called NF-M (Medium); NF200, 200 kD protein also called NF-H (Heavy). In general, there is coordinate expression of all three NF proteins in neurons. The DNA sequences encoding the rat NF200 and NF160 proteins have been cloned (Dautigny, A. et al., 1988, *Biochem. Biophys. Res. Commun.,* 154, 1099–1106 and Napolitano, E. W. et al., 1987, *J. Neurosci.,* 7, 2590–2599, respectively). All three NF protein genes have been cloned in mice and humans. Mouse NF68 nucleic acid sequences were reported in Lewis, S. A. and Cowan, N. J., 1985, *J. Cell Biol.,* 100, 843–850. Mouse NF160 nucleic acid sequences were reported in Levy, E. et al., 1987, *Eur. J. Biochem.,* 166, 71–77. Mouse NF200 nucleic acid sequences were reported in Shneidman, P. S. et al., 1988, *Mol. Brain Res.,* 4, 217–231. In humans, nucleic acid sequences were reported for: NF68, Julien, J.-P. et al., 1987,

*Biochem. Biophys. Acta.,* 909, 10–20; NF160, Myers, M. W. et al., 1987, *EMBO J.,* 6, 1617–1626; NF200, Lee, J. F. et al., 1988, *EMBO J.,* 7, 1947–1955. These DNA sequences are used to produce the protein for the production of antibodies or to isolate other mammalian NF genes and the proteins expressed and antibodies generated for any desired species, as described above for LNGFR. As used herein, the term "NF⁺" means expression of one or more of the three NF proteins.

As used herein, the term "factors permissive for PNS neuronal cell differentiation" means compounds, such as, but not limited to, protein or steroid molecules or substrates such as FN or PDL, which permit at least a neural crest stem cell to become restricted to the PNS neuronal lineage. Such lineage-restricted progeny of neural crest stem cells include PNS neuronal progenitor cells, which are at least bipotential, in that they can divide to give rise to self, as well as, more mature, nondividing PNS neurons.

Mammalian neural crest stem cell compositions are provided which serve as a source for neural crest cell derivatives such as neuronal and glial progenitors of the PNS which in turn are a source of PNS neurons and glia. Methods are provided for the isolation and clonal culture of neural crest stem cells, in the absence of feeder cells. In the examples provided, these methods utilize a chemically defined medium which is supplemented with chick embryo extract as a source of mitogens and survival factors. Factors present in the extract of chicken embryos allow the growth and self renewal of rat neural crest stem cells. However, media used to isolate and propagate rat neural crest stem cells can be used to isolate and propagate neural crest stem cells from other mammalian species, such as human and non-human primates, equines, felines, canines, bovines, porcines, lagomorphs, etc.

Culture conditions provided herein allow the isolation, self-renewal and differentiation of mammalian neural crest stem cells and their progeny. These culture conditions may be modified to provide a means of detecting and evaluating growth factors relevant to mammalian neural crest stem cell self-renewal and the differentiation of the stem cell and its progeny. These modifications include, but are not limited to, changes in the composition of the culture medium and/or the substrate and in the specific markers used to identify either the neural crest stem cell or their differentiated derivatives.

Culture conditions are provided which allow the differentiation of mammalian neural crest stem cells into the PNS neuronal and glial lineages in the absence of feeder cell layers. In addition to liquid culture media, these culture conditions utilize a substratum comprising fibronectin alone or in combination with poly-D-lysine. In the examples provided, human fibronectin is utilized for the culturing of rat neural crest stem cells and their progeny. Human fibronectin can be used for the culturing of neural crest stem cells isolated from avian species as well as from any mammal, as the function of the fibronectin protein is highly conserved among different species. Cells of many species have fibronectin receptors which recognize and bind to human fibronectin.

In order to isolate the subject neural crest stem cells, it is necessary to separate the stem cell from other cells in the embryo. Initially, neural crest cells are obtained from mammalian embryos.

For isolation of neural crest cells from mammalian embryos, the region containing the caudal-most 10 somites are dissected from early embryos (equivalent to gestational day 10.5 day in the rat). These trunk sections are transferred in a balanced salt solution to chilled depression slides, typically at 4° C., and treated with collagenase in an appropriate buffer solution such as Howard's Ringer's solution. After the neural tubes are free of somites and notochords, they are plated onto fibronectin (FN)-coated culture dishes to allow the neural crest cells to migrate from the neural tube. Twenty-four hours later, following removal of the tubes with a sharpened tungsten needle, the crest cells are removed from the FN-coated plate by treatment with a Trypsin solution, typically at 0.05%. The suspension of detached cells is then collected by centrifugation and plated at an appropriate density, generally 225 cells/100 mm dish in an appropriate chemically defined medium. This medium is preferentially free of serum and contains components which permit the growth and self-renewal of neural crest stem cells. The culture dishes are coated with an appropriate substratum, typically a combination of FN and poly-D-lysine (PDL).

Procedures for the identification of neural crest stem cells include incubating cultures of crest cells for a short period of time, generally 20 minutes, at room temperature, generally about 25° C., with saturating levels of antibodies specific for a particular marker, e.g., LNGFR. Excess antibody is removed by rinsing the plate with an appropriate medium, typically L15 medium (Gibco) supplemented with fresh vitamin mix and bovine serum albumin (L-15 Air). The cultures are then incubated at room temperature with a fluorochrome labelled secondary antibody, typically Phycoerythrin R-conjugated secondary antibody (TAGO) at an appropriate dilution for about 20 minutes. Excess secondary antibodies are then removed using an appropriate medium, such as L-15 Air. The plates are then covered with the chemically defined growth medium and examined with a fluorescence microscope. Individual LNGFr⁺ clones are isolated by fluorescence activated cell sorting (FACS) or, more typically, by marking the plate under the identified clone. The markings are typically made to a diameter of 3–4 mm, which generally allows for the unambiguous identification of the progeny of the founder cell at any time during an experiment. If desired, individual LNGFR⁺ clones are removed from the original plate by trypsinization with the use of cloning cylinders.

Procedures for permitting the differentiation of stem cells include the culturing of isolated stem cells in a medium permissive for differentiation to a desired lineage, such as Schwann cell differentiation (SCD) medium. Other procedures include growth of isolated stem cells on substrates capable of permitting differentiation, such as FN or FN and PDL.

Procedures for the serial subcloning of stem cells and their derivatives include the trypsinization of individual clones, as described above, followed by replating the clone on a desired substrate and culturing in a desired medium, such as a chemically defined medium suitable for maintenance of stem cells or SCD medium permissive for the differentiation of said neural crest stem cells. Crest cells may be identified following serial subcloning by live-cell labeling with an antibody directed against LNGFR, as described above.

The methods described herein provide the basis of functional assays which allow for the identification and production of cellular compositions of mammalian cells which have properties characteristic of neural crest stem cells, glial or neuronal progenitor cells or multipotent stem cell precursor of such progenitor cells. In order to isolate such cells from tissues other than embryonic neural tubes, it is necessary to separate the progenitor and/or multipotent stem cells from other cells in the tissue. The methods presented in the examples for the isolation of neural crest stem cells from neural tubes can be readily adapted for other tissues by one skilled in the art. First, a single cell suspension is made from the tissue; the method used to make this suspension will vary depending on the tissue utilized. For example, some tissues require mechanical disruption of the tissue while other tissues require digestion with proteolytic enzymes alone or in combination with mechanical disruption in order to create the single cell suspension. Tissues such as blood already exists as a single cell suspension and no further treatment is required to generate a suspension, although hypotonic lysis of red blood cells may be desirable. Once the single cell suspension is generated it may be enriched for cells expressing LNGFR or other neural cell-specific markers on their surface. One protocol for the enrichment for LNGFR$^+$ cells is by incubating the cell suspension with antibodies specific for LNGFR and isolating the LNGFR$^+$ cells. Enrichment for cells expressing a neural cell-specific surface marker is particularly desirable when these cells represent a small percentage (less than 5%) of the starting population. The isolation of cells which have complexed with an antibody for a neural cell-specific surface marker such as is carried out using any physical method for isolating antibody-labeled cells. Such methods include fluorescent-activated cell sorting in which case the cells, in general, are further labeled with a fluorescent secondary antibody that binds the anti-LNGFR antibody, e.g., mouse anti-LNGFR and fluorescein label goat anti-mouse IgG; panning in which case the antibody-labeled cells are incubated on a tissue-culture plate coated with a secondary antibody; Avidin-sepharose chromatogrphy in which the anti-LNGFR antibody is biotinylated prior to incubation with the cell suspension so that the complexed cells can be recovered on an affinity matrix containing avidin (i.e., where the antibody is an antibody conjugate with one of the members of a binding pair); or by use of magnetic beads coated with an appropriate anti-antibody so that the labeled LNGFR-expressing cells can be separated from the unlabeled cells with the use of a magnet. All of the foregoing cell isolation procedures are standard published procedures that have been used previously with other antibodies and other cells.

The use of antibodies specific for neural stem-cells specific surface markers is expected to result in the isolation of multipotent neural stem cells from tissues other than embryonic neural tubes. For example, as previously indicated, LNGFR is expressed in cells of the ventricular zone throughout the embryonic central nervous system of the rat and chick. This implies that other mammalian species have a similar pattern of LNGFR expression and studies in human with monoclonal antibodies against the human LNGFR (Loy, et al. (1990) *J. Neurosci. Res.* 27, 651–654) are consistent with this expectation. Since cells from the ventricular zone (Cattaneo and McKay (1991) *Trends Neurosci* 14, 338–340; Reynolds and Weiss (1992) *Science* 255, 1707–1710) are likely to be stem cells (Hall & Watt (1989) *Development* 106, 619–633; Potter & Loeffer (1990) *Development* 110, 1001–1020) antibodies to neural cell-specific surface markers should prove useful in isolating multipotent neural stem cells from the central and peripheral nervous systems and potentially from other tissue sources.

Alternatively, or in conjunction with the above immunoisolation step, the cells are plated at clonal density, generally 225 cells/100 mm dish, in an appropriate chemically defined medium on a suitable substrate as described in the examples for isolation of rat neural crest stem cells. The presence of neural crest-like stem cells (e.g., a multipotent neural stem cell) is confirmed by demonstrating that a single cell can both self-renew and differentiate to members of at least the PNS neuronal and glial lineages utilizing the culture conditions described herein. Other types of multipotent neural stem cells are identified by differentiation to other cell type such as CNS neural or glial cells or their progenitors. Depending upon the source of the tissue used in the foregoing methods, multipotent neural stem cells may not be obtained. Rather, further differentiated cell types such as glial and neuronal progenitor cells may be obtained.

Transplantation assay systems described herein provide the basis of functional assays which allow for the identification of mammalian cells which have properties characteristic of neural crest stem cells, multipotent neural stem cells and/or neuronal or glial progenitor cells. Cells of interest, identified by either the in vivo or in vitro assays described above, are transplanted into mammalian hosts using standard surgical procedures. The transplanted cells and their progeny are distinguished from the host cells by the presence of species specific antigens or by the expression of an introduced marker gene. The transplanted cells and their progeny are also stained for markers of mature neurons and glia in order to examine the developmental potential of the transplanted cells. This transplantation assay provides a means to identify neural crest stem cells by their functional properties in addition to the in vitro culture assays described above.

Additionally, the transplantation of cells having characteristics of multipotent neural stem cells, neural crest stem cells or progenitors of neuronal or glial cells provides a means to investigate the therapeutic potential of these cells for neurological disorders of the PNS and CNS in animal models. Examples of PNS disorders in mice include the trembler and shiverer strains. The trembler mutation is thought to involve a defect in the structural gene for myelin basic protein (MBP). This mutation maps to the same region of chromosome 11 as does the MBP gene. This mutation results in the defective myelination of axons in the PNS. An analogous disorder is seen in humans, Charcot-Marie-Tooth syndrome, which results in progressive neuropathic muscular atrophy.

The shiverer mutation in mice results in a severe myelin deficiency throughout the CNS and a moderate hypomyelination in the PNS. Severe shivering episodes are seen 12 days after birth. An analogous disorder is seen in humans, Guillaum-Barre' disease, which is characterized by an acute febrile polyneuritis.

Cells having characteristics of multipotent neural stem cells, neural crest stem cells or neuronal or glial progenitors of the PNS or CNS (identified by either in vitro or in vivo assays) are introduced into a mammal exhibiting a neurological disorder to examine the therapeutic potential of these cells. These cells are preferably isolated from a mammal having similar MHC genotypes or the host mammal is immunosuppressed using drugs such as cyclosporin A. The cells are injected into an area containing various peripheral nerves known to be effected in a particular mammal or into the spinal cord or brain for mammals which show involvement of the CNS. The cells are injected at a range of concentrations to determine the optimal concentration into the desired site. Alternatively, the cells are introduced in a plasma clot or collagen gel to prevent rapid dispersal of cells from the site of injection. The effect of this treatment on the neurological status of the model animal is noted. Desired therapeutic effects in the above mutant mice include the reduction or cessation of seizures or improved movement of lower motor extremities.

There is strong interest in identifying the multipotent neural stem cells such as the neural crest stem cell and defining culture conditions which allow the clonal propagation and differentiation of said stem cells. Having possession of a multipotent neural stem cell or a neural crest stem cell allows for identification of growth factors associated with self regeneration. In addition, there may be as yet undiscovered growth factors associated with (1) with the early steps of restriction of the stem cell to a particular lineage; (2) the prevention of such restriction; and (3) the negative control of the proliferation of the stem cell or its derivatives.

The multipotent neural stem cell or neural crest stem cell are useful to: (1) detect and evaluate growth factors relevant to stem cell regeneration; (2) detect and evaluate other growth factors relevant to differentiation of stem cell derivatives, such as neurons and glia; (3) produce various neural stem cell derivatives, including both the progenitors and mature cells of a given lineage and (4) provide a source of cells useful for treating neurological diseases of the PNS and CNS in model animal systems and in humans. The culture conditions used herein allow for the growth and differentiation of stem cells in vitro and provide a functional assay whereby mammalian tissues can be assayed for the presence of cells having the characteristics of neural stem cells. The transplantation assay described herein also provides a functional assay whereby mammalian neural stem cells may be identified.

As indicated in the examples, neural crest stem cells have been passaged for at least six-ten generations in culture. Although it may be unnecessary to immortalize those or other stem cell lines or progenitor cell lines obtained by the methods described herein, once a cell line has been obtained it may be readily immortalized to yield a continuously growing cell line useful for screening trophic or differentiation factors or for developing experimental transplantation therapies in animals. Such immortalization can be obtained in neural stem cells or progenitors of glial and neuronal cells by genetic modification of such cells to introduce an immortalizing oncogene such as v-myc. It has already been demonstrated that retrovirally-transduced v-myc can be used to generate immortal cell lines from other neural crest-derived cell populations. (Birren and Andersen (1990) *Neuron* 4, 189–201; Lo, et al., (1990) *Deval. Biol.* 145, 139–153). In addition, other oncogenes such as those from viruses, e.g., SV40-T antigen (Fredericksen, et al., (1988) *Neuron* 1, 439–448) can also be used. Such immortilization is preferably performed prior to differentiation of the isolated neural stem or progenitor cells.

The following is presented by way of example and is not to be construed as a limitation on the scope of the invention. Further, all references referred to herein are expressly incorporated by reference.

EXAMPLES

Example 1

Preparation of Neural Crest Cells

For a given preparation 5–10 timed pregnant female Sprague-Dawley rats (Simonson Laboratories, Gilroy, Calif.) were killed by $CO_2$ asphyxiation. Embryos were removed and placed into Hank's Balanced Salt Solution (HBSS) (GIBCO, Grand Island, N.Y.) at 4° C. for 2–4 hours. Under a dissecting microscope, at room temperature, a block of tissue from a region corresponding to approximately the caudal most 10 somites was dissected from each embryo using an L-shaped electrolytically sharpened tungsten needle. Trunk sections were transferred in HBSS into one well of a 3 well depression slide that had been chilled to 4° C. Trunk sections were treated with collagenase (152 units/mg) (Worthington Biochemical, Freehold, N.J.) made to a concentration of 0.75 mg/ml in Howard's Ringer's solution (per 1 liter of $dH_2O$: NaCl 7.2 g; $CaCl_2$ 0.17 g; KCl 0.37 g) and sterilized, by passage through a 0.22 μm filter prior to use. The collagenase solution was exchanged at least 3 times and with each exchange the trunk sections were vigorously triturated by passage through a pasteur pipet. After incubation at 37° C. for 20 minutes in humidified $CO_2$ atmosphere, the trunk sections were triturated very gently until most of the neural tubes were free and clean of somites and notochords. The collagenase solution was quenched by repeated exchanges with cold complete medium (described below). The neural tubes were plated onto fibronectin-coated (substrate preparation is described below) 60 mm tissue culture dishes (Corning, Corning, N.Y.) that had been rinsed with complete medium. After a 30 minute incubation to allow the neural tubes to attach, dishes were flooded with 5 ml of medium. After a 24 hour culture period, using an L-shaped electrolytically sharpened tungsten needle and an inverted phase contrast microscope equipped with a 4× objective lens, each neural tube was carefully scraped away from the neural crest cells that had migrated onto the substrate. Crest cells were removed by a 2 minute 37° C. treatment with 0.05% Trypsin solution (GIBCO). The cells were centrifuged for 4 minutes at 2000 r.p.m. and the pellet was resuspended into 1 ml of fresh complete medium. Typically the cells were plated at a density of 225 cells/100 mm dish.

Substrate Preparation
A. Fibronectin (FN) Substrate.

Tissue culture dishes were coated with human plasma fibronectin (New York Blood Center, New York, N.Y.) in the following way. Lyophilized fibronectin was resuspended in sterile distilled water ($dH_2O$) to a concentration of 10 mg/ml and stored at −80° C. until used. The fibronectin stock was diluted to a concentration of 250 mg/ml in Dulbecco's phosphate buffered saline (D-PBS) (GIBCO). The fibronectin solution was then applied to tissue culture dishes and immediately withdrawn.
B. Poly-D-Lysine (PDL) and FN Substrate.

Sterile poly-D-Lysine (PDL) was dissolved in $dH_2O$ to as concentration of 0.5 mg/ml. The PDL solution was applied to tissue culture plates and immediately withdrawn. The plates were allowed to dry at room temperature, rinsed with 5 ml of $dH_2O$ and allowed to dry again. Fibronectin was then applied, as described above, over the PDL.

Example 2

Development of a Defined Medium for the Growth of Rat Neural Crest Stem Cells.

A serum-free, chemically defined basal medium was developed based on the formulations of several existing defined media. This basal medium consists of L15-$CO_2$ formulated as described by Hawrot, E. and Patterson, P. H., 1979, *Methods in Enzymology*, 58, 574–583 supplemented with additives described by Bottenstein, J. E. and Sato, G. H., 1979, *Proc. Natl. Acad. Sci. USA*, 76, 514–517 and further supplemented with the additives described by Sieber-Blum, M. and Choksbi, 1985, *Exp. Cell Res.*, 158, 267–272. The final recipe is given here: to L15-$CO_2$ add, 100 μg/ml transferrin (Calbiochem, San Diego, Calif.), 5 μg/ml insulin (Sigma, St. Louis, Mo.), 16 μg/ml putrescine (Sigma), 20 nM progesterone (Sigma), 30 nM selenious acid (Sigma), 1 mg/ml bovine serum albumin, crystallized (GIBCO), 39 pg/ml dexamethasone (Sigma), 35 ng/ml retinoic acid (Sigma), 5 μg/ml a-d, 1-tocopherol (Sigma), 63 μg/ml p-hydroxybuyrate (Sigma), 25 ng/ml cobalt chloride (Sigma), 1 μg/ml biotin (Sigma), 10 ng/ml oleic acid (Sigma), 3.6 mg/ml glycerol, 100 ng/ml α-melanocyte stimulating hormone (Sigma), 10 ng/ml prostaglandin El (Sigma), 67.5 ng/ml 35 triiodothyronine (Aldrich Chemical Company, Milwaukee, Wis.), 100 ng/ml epidermal growth factor (Upstate Biotechnology, Inc., Lake Placid, N.Y.), 4 ng/ml bFGF (UBI), and 20 ng/ml 2.55 NGF (UBI).

To allow the growth and regeneration of neural crest stem cells in feeder cell-independent cultures, it was necessary to supplement the basal medium with 10% chick embryo extract (CEE). This supplemented medium is termed complete medium.

CEE is prepared as follows: chicken eggs were incubated for 11 days at 38° C. in a humidified atmosphere. Eggs were washed and the embryos were removed, and placed into a petri dish containing sterile Minimal Essential Medium (MEM with Glutamine and Earle's salts) (GIBCO) at 4° C. Approximately 10 embryos each were macerated by passage through a 30 ml syringe into a 50 ml test tube (Corning). This typically produced 25 ml of volume. To each 25 ml was added 25 ml of MEM. The tubes were rocked at 4° C. for 1 hour. Sterile hyaluronidase (1 mg/25 g of embryo) (Sigma) was added and the mixture was centrifuged for 6 hours at 30,000 g. The supernatant was collected, passed first through a 0.45 μm filter, then through a 0.22 μm filter and stored at −80° C. until used.

At the low cell densities necessary for survival and proliferation of individual neural crest cells, either fetal calf serum (FCS, JR Scientific) or CEE was required, in addition to the basal medium, for clone formation. When FCS was used to supplement the medium, it was heat inactivated by treatment at 55° C. for 30 minutes. FCS was stored at −20° C. and passed through a 0.22 um filter prior to use.

CEE is preferred as a supplement, as in the presence of FCS, most of the cells derived from the neural crest exhibit a flattened, fibroblastic morphology and expression of LNGFR is extinguished. In the absence of both FCS and CEE, clone formation from neural crest cells was greatly attenuated.

Example 3

Isolation and Cloning of Multipotent Rat Neural Crest Cells.

A. Identification of Antibody Markers Expressed by Neural Crest Cells.

In order to identify and isolate rat neural crest cells, it was necessary to identify antibody markers that could be used to recognize these cells. When E10.5 neural tubes were explanted onto a fibronectin (FN) substratum, many of the neural crest cells that emigrated from the neural tubes over the next 24 hours expressed the low-affinity NGF receptor (LNGFR), recognized by monoclonal antibodies 192-Ig and 217c. The outgrowth of neural crest cells from the dorsal side of the explanted neural tube following 24 hours growth in culture is shown in FIG. 1, panel A. FIG. 1, panel B shows the expression of LNGFR (green florescence) and nestin (red fluorescence) in neural crest cells.

Neural crest cells were labeled with antibodies as follows: For cell surface antigens, such as LNGFR, it was possible to label the living cells in culture. The cultures were incubated with primary antibody solution for 20 minutes at room temperature. The cultures were washed twice with L15 medium (GIBCO) supplemented with 1:1:2, fresh vitamin mix (FVM) (Hawrot, E. and Patterson, P. H., 1979, ibid), and 1 mg/ml bovine serum albumin (L-15 Air). The cultures were then incubated for 20 minutes at room temperature with Phycoerythrin R conjugated secondary antibody (TAGO) at a dilution of 1:200 in L-15 Air. The cultures were then rinsed twice with L-15 Air and placed back in their original medium and examined with a fluorescence microscope. Rabbit anti-LNGFR antiserum (Weskamp, G. and Reichardt, L. F., 1991, Neuron, 6, 649–663) was a kind gift of Gisela Weskamp, University of California, San Francisco and was used at a 1:1000 dilution. Monoclonal anti-NCAM antibody 5A5 (Dodd, J. et al., 1988, Neuron, 1, 105–116) and monoclonal anti-sulfatide antibody $O_4$ (Sommer, I. and Schachner, M. 1981, Dev. Biol. 83, 311–327) were obtained as hybridoma cells from the Developmental Studies Hybridoma Bank (Johns Hopkins Univ., Baltimore, Md.) and prepared as described by the provider.

In order to label cells with antibodies directed against intracellular proteins, it was necessary to fix and permeabilize the cells prior to labeling. For most of the immunocytochemistry, formaldehyde fixation was done. Formaldehyde solution 37% was diluted 1:10 into S-MEM with 1 mM HEPES buffer (GIBCO). Culture were treated for 10 minutes at room temperature with the 3.7% formaldehyde solution and then rinsed 3 times with D-PBS (GIBCO).

For some intermediate filament proteins (NF and GFAP) formaldehyde fixation was not possible. Cultures were fixed by treatment with a solution of 95% ethanol and 5% glacial acetic acid at −20° C. for 20 minutes.

For the staining of cytoplasmic antigens, fixed cells were first treated with a blocking solution comprising D-PBS, 0.1% Tween-20 (Bio-Rad Laboratories, Richmond, Calif.) and 10% heat inactivated normal goat serum (NGS) for 15 minutes at room temperature. Primary antibodies were diluted with a solution of D-PBS, 0.1% Tween-20 and 5% NGS. The fixed cells were incubated overnight at 4° C. in primary antibody solution then rinsed twice with D-PBS, 0.05% Tween-20. Fluorescent secondary antibodies were diluted with D-PBS, 1% NGS and applied to cells for 1 hour at room temperature. The cells were rinsed twice with D-PBS, 0.05% Tween-20. To prevent photobleaching, a solution of 8 mg/ml N-propyl gallate in glycerol was placed over the stained cells prior to fluorescence microscopy.

Mouse monoclonal anti-GFAP, G-A-5 (Debus et al., 1983, Differentiation, 25, 193–203) was purchased from Sigma and used at a 1:100 dilution. Mouse monoclonal anti-NF200, SMI39 was purchased from Sternberger Monoclonals Inc., Baltimore, Md. and used at a 1:100 dilution. SMI39 reactivity is equivalent to the 06-53 monoclonal antibody described by Sternberger, L. A. and Sternberger, N. H., 1983, Proc. Natl. Acad. Sci. USA, 80, 6126–6130. Purified rabbit antibodies to peripherin (preparation 199-6) was obtained from Dr. Linda Parysek, Univ. of Cincinatti, Ohio and was used at a dilution of 1:500.

Flow-cytometric analysis indicated that greater than 70% of the neural crest cells show some LNGFR immunoreactivity (FIG. 1, panel D). Approximately 25% of the neural crest cells expressed high levels of LNGFR. In some experiments, neural crest cells expressing high levels of LNGFR were further purified by labeling with 192-Ig (anti-LNGFR) and fluorescence-activated cell sorting (FACS). For single cell analysis, however, it proved more convenient to plate the bulk neural crest cell population at clonal density, and then subsequently identify LNGFR-positive cells by live cell-labeling with 192-Ig.

Most or all of the neural crest cells also expressed nestin, an intermediate filament protein found in CNS neuroepithelial cells. An individual neural crest cell co-expressing both nestin and LNGFR is shown in FIG. 2, panels A–C. Panel A shows the individual neural crest cell in phase contrast. Panels B and C show this cell following staining with both anti-LNGFR (panel B) and anti-nestin (panel C). FIG. 2, panels D–F show that the clonal progeny of this nestin$^+$, LNGFR$^+$ neural crest cell also coexpress nestin and LNGFR.

B. Cloning of Multipotent Neural Crest Cells

To define the developmental potential of individual neural crest cells, conditions were established that permit the growth of these cells in clonal culture. FIG. 3 provides a flow chart depicting the following cell cloning experiments. In FIG. 3, plating medium refers to the complete medium, described above and differentiation medium refers to SCD medium, described below. Using an FCS-free, CEE-containing medium (complete or plating medium), single neural crest cells (FIG. 4, panel A, phase contrast and panel B, LNGFR staining) were plated on a FN/PDL substratum and allowed to proliferate and differentiate. After 9–14 days, many of the clones founded by single neural crest cells were large and contained cells with a neuronal morphology (FIG. 4, panel C, phase contrast). Quantification indicated that >60% of the clones contained a mixture of neuronal and non-neuronal cells (see below). These neuronal cells could be labeled by antibodies to pan-neuronal markers such as neurofilament (FIG. 4, panel E, anti-NF160 staining) and high-polysialyic acid (PSA) NCAM (FIG. 4, panel D, anti-NCAM staining), as well as by an antibody to peripherin, an intermediate filament protein that is preferentially expressed by peripheral nervous system (PNS) neurons (FIG. 4, panel F). Importantly, these neurons did not express either nestin or LNGFR, indicating that they have lost the two markers that characterize the undifferentiated neural crest cell.

The neuron-containing clones also contained non-neuronal cells. These cells continued to express LNGFR and nestin, in contrast to the neurons, and displayed an elongated morphology characteristic of Schwann cells. While immature Schwann cells are known to express both LNGFR and nestin, these markers are insufficient to identify Schwann cells in this system since they are expressed by the neural crest precursor cell as well. Expression of more definitive Schwann cell markers was elicited by transferring the cells into a medium known to enhance Schwann cell differentiation. This medium, called Schwann cell differentiation (SCD) medium, contained both 10% FCS and 5 $\mu$M forskolin, an activator of adenylate cyclase.

FIG. 5 shows the expression of a Schwann cell phenotype by neural crest-derived glia. Clones plated initially on FN were allowed to grow for a week in complete medium, then transferred into SCD medium and allowed to grow for another 1–2 weeks prior to fixation and immunocytochemistry. Cells of two morphologies, one elongated and the other flattened can be seen in phase contrast (Panels A and D). To demonstrate concordant expression of three markers, LNGFR, O$_4$ and GFAP, two different double-labeling experiments were performed. Living cells were surface-labeled with monoclonal anti-LNGFR 192IgG (Panel B) and monoclonal O$_4$ IgM (Panel C) and postfixed. In parallel, other cells from the same clone were first surface-labeled with O$_4$ and then fixed with acid-ethanol, permeabilized and stained with anti-GFAP (IgG). Note that LNGFR$^+$ cells (Panel B) are O$_4^+$ and that most or all of the O$_4^+$ cells are also GFAP$^+$ (Panels E and F). The quality of the O$_4$ staining in (Panel E) appears different from that in (Panel C) because a redistribution of the antigen occurs following acid-ethanol fixation. In Panel C, the flattened O$_4^+$ cells are more weakly stained for LNGFR (Panel B). Such flattening is indicative of myelination, and is consistent with the fact that Schwann cells undergoing myelination down-regulate LNGFR and up-regulate O$_4$.

Following 5–10 days in SCD medium, most or all of the non-neuronal cells in the clones expressed glial fibrillary acidic protein (GFAP), an intermediate filament specific to glial cells, and sulfatide, a cell-surface glycolipid recognized by the monoclonal antibody O$_4$. Triple-labeling of such "mature" clones with polyclonal anti-peripherin and monoclonal O$_4$ and anti-GFAP antibodies revealed that sulfatide and GFAP were not expressed by the peripherin-positive neurons and that these two glial markers were coincident in the non-neuronal cell population (FIG. 6). FIG. 6 shows a clone from a single founder cell in phase contrast (Panel A) which expresses LNGFR (Panel B). This clone was allowed to proliferate and differentiate in complete medium (containing CEE and lacking serum) and then transferred into SCD medium (containing serum and forskolin). After approximately 10 days, the culture was fixed and triple-labeled with rabbit anti-peripherin (Panels C and D, in green/yellow), anti-GFAP (IgG) (Panel C, in red) and O$_4$ (IgM) (Panel D, blue). Panels C and D are two separate fields from the same clone.

Although GFAP is expressed by astrocytes and sulfatide is expressed by oligodendrocytes in the CNS, the co-expression of these two markers in the same cell is unique to peripheral glial cells (Jessen, K. R. et al., 1990, *Devel.*, 109, 91–103 and Mirsky, R. et al., 1990, *Devel.*, 109, 105–116).

Therefore, these data indicate that single neural crest cells expressing nestin and LNGFR are able to give rise to clones of differentiated cells containing both peripheral neurons and glia. Differentiation to the neuronal phenotype involves both the loss of LNGFR and nestin expression, and the gain of neuronal markers such as neurofilament, high PSA-NCAM and peripherin. On the other hand, in the glial lineage LNGFR and nestin expression persist, and additional glial markers (GFAP and O$_4$) are acquired. All clones that produced neurons and glia also produced at least one other cell type that did not express any of the differentiation markers tested; the identity of these cells is unknown. Taken together, these data establish the multipotency of the rat neural crest cell identified and isolated by virtue of co-expression of LNGFR and nestin.

Example 4

Self-renewal of multipotent neural crest cells in vitro

After 10 days in culture in medium supplemented with 10% CEE and on a FN/PDL substrate, all of the neural crest cell clones that contained neurons also contained non-neuronal cells expressing LNGFR and nestin (as described above). In order to determine whether these cells were immature glia, or multipotent neural crest cells that had undergone self-renewal, serial subcloning experiments were performed. FIG. 7 provides a flow chart summarizing these serial subcloning experiments. In FIG. 7, "plating medium" refers to complete medium containing CEE and lacking FCS and "differentiation medium" refers to SCD medium containing FCS and forskolin.

For serial sub-cloning experiments, clones were harvested and replated as follows. The primary clones were examined microscopically to ensure that there were no impinging colonies and that the whole clone fits within the inscribed circle. Using sterile technique throughout the procedure, glass cloning cylinders (3 mm id.) were coated on one end with silicone grease (Dow-Corning) and placed about the primary clone so that the grease formed a seal through which medium could not pass. The cells were removed from the cylinder by first treating them with 100 ml of 0.05% Trypsin solution (GIBCO) for 3 minutes at 37° C. in a humidified 5% $CO_2$ incubator. At room temperature 70 µl of the trypsin solution was removed and replaced with 70 µl of complete medium. The cells were resuspended into the 100 µl volume by vigorous trituration through a pipet tip and the whole volume was diluted into 5 ml of complete medium. The 5 ml was then plated onto 1 or 2 60 mm dishes which were placed in a humidified 5% $CO_2$ incubator for 2 hours at which time the medium was exchanged for fresh complete medium. Single founders cells were then identified and allowed to grow into secondary clones as described below.

Primary clones founded by LNGFR-positive progenitor cells were allowed to grow for 6 days (FIG. 8, Panel A) on a PDL/FN substrate. At this time, clones containing LNGFR-positive cells were identified by live cell surface labeling, and these clones were then removed from their original plates by trypsinization, as described above. The dissociated cells were then replated at clonal density under the same culture conditions as their founder cells. Individual secondary founder cells were identified by labeling live cells with 192-Ig and their positions marked (FIG. 8, Panels B and B' show two individual secondary founder cells; Panels C and C' show the clonal progeny of these individual cells at day 17). Both non-neuronal, neurite bearing cells are visible in the clones (FIG. 8, panels C and C').

A clone derived from secondary founder cells, such as that shown in FIG. 8, was transferred into SCD medium to allow the expression of Schwann cell markers. After approximately 10 days, the subclone was fixed, and double-labeled for NF160 and GFAP (FIG. 9, Panel A shows the clone in phase contrast; Panel B shows labeling with anti-NF160; Panel C shows labeling with anti-GFAP). The apparent labeling of neurons in panel C is an artifact due to bleed-through into the fluorescein channel of the Texas Red fluorochrome used on the goat anti-rabbit secondary antibody in panel B.

Additionally, following 10 days of secondary culture, living subclones were scored visually for the presence of neurons and glia by double labeling with 192-Ig (anti-LNGFR) and 5A5, a monoclonal antibody to high PSA-NCAM.

Single neural crest cells isolated from primary clones were able to proliferate and generate clones containing both neurons and non-neuronal cells, probably glia. Quantitative analysis of clones derived from 16 different primary and 151 secondary founders after ten days in plating medium indicated that over 30% of the total secondary founder cells gave rise to clones containing neurons (N), glia (G) and other (O) cells (Table I., N+G+O). Of the remaining 70% of the founder cells, however, almost 50% failed to form clones and died; thus of the clonogenic (i.e., surviving) founders, 54% were of the N+G+O type (Table I). To confirm that these mixed clones indeed contained glia or glial progenitors, they were transferred to SCD medium and allowed to develop for an additional 7 days, then fixed and double-stained for neurofilament and GFAP expression. As was the case for the primary clones, this treatment caused expression of GFAP in a high proportion of non-neuronal cells in the clones (FIG. 9), confirming the presence of glia. These data indicate that primary neural crest cells are able to give rise at high frequency to progeny cells retaining the multipotency of their progenitors, indicative of self renewal. However, in several cases secondary clones containing only neurons were found (Table I, N only), and many of the secondary clones contained glia and other cells but not neurons (Table I, G+O). This observation suggests that in addition to self-renewal, proliferating neural crest cells may undergo lineage restriction in vitro as well to give rise to glial or neuronal progenitor cells which are characterized by the capacity to divide and self-renew but are restricted to either the neuronal or glial lineage.

TABLE I

| Primary Clone ID | # of 2° Founders | Sub-Clone Phenotype total # (%) | | | | No clone found |
|---|---|---|---|---|---|---|
| | | N only | N + G + O | G + O | O | |
| 1.1 | 21 | 0 | 15 (71) | 0 | 0 | 6 (29) |
| 1.18 | 6 | 0 | 1 (17) | 1 (17) | 2 (33) | 2 (33) |
| 1.24 | 5 | 1 (20) | 0 | 1 (20) | 2 (40) | 1 (20) |
| 2.6 | 7 | 0 | 0 | 1 (14) | 1 (14) | 5 (72) |
| 2.18 | 7 | 0 | 0 | 1 (14) | 0 | 6 (86) |
| 3.14 | 20 | 0 | 2 (10) | 4 (20) | 0 | 14 (70) |
| 3.18 | 4 | 0 | 1 (25) | 0 | 0 | 3 (75) |
| 4.5 | 1 | 0 | 1 (100) | 0 | 0 | 0 |
| 4.8 | 9 | 0 | 0 | 1 (11) | 2 (22) | 6 (67) |
| 4.14 | 10 | 0 | 2 (20) | 3 (30) | 1 (10) | 4 (40) |
| 5.2 | 15 | 1 (7) | 8 (53) | 0 | 0 | 6 (40) |
| 6.1 | 13 | 0 | 2 (15) | 2 (15) | 0 | 9 (70) |
| 6.2 | 17 | 1 (6) | 2 (12) | 4 (24) | 0 | 10 (58) |
| 6.17 | 2 | 0 | 1 (50) | 0 | 0 | 1 (50) |
| 8.2 | 5 | 0 | 4 (80) | 0 | 0 | 1 (20) |
| 8.5 | 9 | 0 | 4 (44) | 0 | 0 | 5 (56) |
| Mean ± s.e.m. | | | | | | |
| % total founders | | 2.1 ± 1.3 | 31 ± 7.9 | 10 ± 2.6 | 7.4 ± 3.3 | 49 ± 6 |
| % clonogenic founders | | 3.1 ± 1.8 | 54 ± 11 | 29 ± 8 | 15 ± 6 | |

Example 5

Substrate Composition Influences the Developmental Fate of Multipotent Neural Crest Cells The foregoing experiments indicate that neural crest cells grown on a PDL/FN substrate generate clones containing both peripheral neurons and glia. When the same cell population is grown at clonal density on a substrate containing FN only, the resulting clones contain glia and "other" cells but never neurons (FIGS. 10 and 11, Panels D,E,F). FIG. 10 provides a flow chart summarizing the following experiments which demonstrate the substrate effect on the fate of mammalian neural crest cells. FIG. 11 shows the immunoreactivity of cells stained for various markers.

On FN alone, G+O clones are obtained containing non-neuronal cells expressing high levels of LNGFR immunoreactivity, but neither NCAM$^+$ nor neurite-bearing cells (FIG. 11, panels E,F). By contrast on PDL/FN, the clones contain both LNGFR+, NCAM non-neuronal crest cells and LNGFR−, NCAM$^+$ neurons (FIG. 11, panels B,C). Quantification indicated that on FN alone, 70–80% of the clones are of the G+O phenotype and none of the N+G+O phenotype (FIG. 12, panel A), whereas on PDL/FN 60% of the clones are of the N+C+O and only 20% are of the G+O phenotype (FIG. 12, panel B). These data indicate that the composition of the substrate affects the phenotype of neural crest cells that develop in culture.

To rule out the possibility that the foregoing results could be explained simply by the failure of neurogenic crest cells to adhere and survive on a FN substrate, a different experiment was performed in which all the crest cells were initially cloned on a FN substrate. FIG. 13 provides a flow chart summarizing these experiments. These experiments were performed to demonstrate that differences in attachment and/or survival do not account for differences in eventual clone composition. Subsequently, one group of cells was exposed to PDL as an overlay (that is, PDL was added to the liquid media to a final concentration of 0.05 mg/ml rather than being immobilized on the culture dish) after 48 hrs, while a sister culture was retained on FN alone as a control (FIG. 13). Clones expressing LNGFR were identified by live cell surface labeling at the time of the PDL overlay and the development of only LNGFR+ clones was further monitored. After two weeks, the cultures were transferred to SCD medium for an additional 10 days of culture, and their phenotypes then scored as previously described.

By contrast to clones maintained on FN, where no neurons developed, many of the clones exposed to a PDL overlay contained neurons at the end of the culture period (FIG. 14, panel A). Moreover, virtually none of the clones were of the G+O phenotype after the PDL overlay. These data indicate that an overlay of PDL is able to alter the differentiation of neural crest cells even if they are initially plated on an FN substrate. Moreover, they suggest that at least some of the N+G+O clones derived by conversion of founder cells that would have produced G+O clones on FN. However, because of the increased cytotoxicity obtained from the PDL overlay, it was not possible to rule out the possibility that many of the cells that would have produced G+O clones simply died. To address this issue, the PDL overlay was performed on a parallel set of cultures at day 5 rather than at 48 hrs. Under these conditions, virtually all of the LNGFR+ clones survived and differentiated. 60% of these clones contained neurons, whereas 35% contained G+O (FIG. 14, panel B). By contrast, greater than 90% of the clones maintained on FN developed to a G+O phenotype. Since little or no clone death was obtained under these conditions, and since a majority of the clones contained neurons following the PDL overlay at day 5, these data suggest that PDL converts presumptive G+O clones into N+G+O clones. However the fact that 35% of the clones became G+O following PDL overlay at days, whereas virtually none did so when the overlay was performed at 48 hrs (FIG. 14, compare G+O, hatched bars, in panels A and B), suggests that some clones might become resistant to the effect of PDL between 48 hrs and days.

Example 6

Substrate Influences Latent Developmental Potential of Neural Crest Cells

To demonstrate more directly that the substrate can alter the developmental fate of neural crest cells, a serial subcloning experiment was performed. Clones were established on FN, and after 5 days the progeny of each clone were subdivided and cloned onto both FN and PDL/FN substrates. Following 10 days of culture in standard medium, the clones were shifted to SCD medium for an additional week to ten days and then fixed, stained and scored for the presence of neurons and Schwann cells. Five of seven primary clones founded on FN gave rise to secondary clones containing neurons when replated onto a PDL/FN substrate at days (Table II). On average, 57±17% of the secondary clones contained neurons. By contrast, none of the sister secondary clones replated onto FN contained neurons (Table II). These data confirm that the PDL/FN substrate is able to alter the fate of neural crest cell clones initially grown on FN. They also reveal that the "neurogenic potential" of neural crest cells is retained, at least for a period of time, on FN even though overt neuronal differentiation is not observed. This suggested that FN is non-permissive for overt neuronal differentiation under these culture conditions. In support of this idea, when primary clones established on PDL/FN were replated onto FN, none of the secondary clones contained neurons, whereas 100% (5/5) of the primary clones gave rise to neuron-containing secondary clones when replated onto PDL/FN (Table II). Moreover, on average 93±7% of the secondary clones derived from each primary clone contained neurons on PDL/FN, indicating that most or all of the clonogenic secondary crest cells retained neurogenic potential under these conditions.

While this experiment indicated that at least some neural crest clones retain neurogenic potential on FN, not all clones exhibited this capacity. This could indicate a heterogeneity in the clonogenic founder cells that grow on FN, or it could indicate a progressive loss of neurogenic potential with time in culture on FN. To address this issue, a second experiment was performed in which primary clones were replated at day 8 rather than at day 5. In this case, a more dramatic difference was observed between primary clones established on FN versus on PDL/FN. Only 1/6 primary FN clones replated at day 8 gave rise to any secondary clones containing neurons on PDL/FN, and in this one case only 17% of the secondary clones contained neurons (Table II). By contrast, 6/6 primary PDL/FN clones gave rise to neuron-containing secondary clones when replated on PDL/FN at day 8, and 52±7% of these secondary clones contained neurons (Table II). These data suggest that neurogenic potential is gradually lost by neural crest cells cultured on FN, but retained to a much greater extent by the same cells grown on PDL/FN. Thus the composition of the substrate influences not only the overt differentiation of the neural crest cells, but also their ability to maintain a latent developmental potential over multiple cell generations.

TABLE II

| 1° Substrate | FN | | % | pDL/FN | | % |
|---|---|---|---|---|---|---|
| 2° Substrate | FN | pDL/FN | Neuronal | FN | pDL/FN | Neuronal |
| Day 5 Replating | 0/7 | 5/7 | 57 ± 17 | 0/5 | 5/5 | 93 ± 7 |
| Day 8 Replating | 0/6 | 1/6 | 17 | 0/6 | 6/6 | 52 ± 7 |

Example 7

Identification of neural crest stem cells by transplantation

Neural crest stem cells are identified by two general criteria: by their antigenic phenotype, and by their functional properties. These functional properties may be assessed in culture (in vitro), as described above, or they may be assessed in an animal (in vivo). The above examples described how the self-renewal and differentiation of neural crest stem cells can be assayed in vitro, using clonal cell cultures. However, these properties may also be determined by transplanting neural crest cells into a suitable animal host. Such an assay requires a means of delivering the cells and of identifying the transplanted cells and their progeny so as to distinguish them from cells of the host animal. Using standard techniques, it is possible to deliver neural crest cells to a developing mammalian or avian embryo or to any tissue or compartment of the adult animal (e.g., brain, peritoneal cavity, etc.).

For example, neural crest cell cultures are prepared as described earlier. After a suitable period in primary or secondary culture, neural crest cells are identified by live cell-labeling with antibodies to LNGFR, and removed from the plate using trypsin and a cloning cylinder, as described in previous examples. The cells are diluted into serum-containing medium to inhibit the trypsin, centrifuged and resuspended to a concentration of $10^6$–$10^7$ cells per milliliter. The cells are maintained in a viable state prior to injection by applying them in small drops (ca. 10 $\mu$l each) to a 35 mm petri dish, and evaporation is prevented by overlaying the droplets with light mineral oil. The cells are kept cold by keeping the petri dishes on ice. For injections into mouse embryos, pregnant mothers at embryonic day 8.5–9.0 are anaesthetized and their uterus exposed by an incision into the abdomen. Neural crest cells are drawn into a sharpened glass micropipette (with a sealed tip and hole in the side to prevent clogging during penetration of tissues) by gentle suction. The pipette is inserted into the lower third of the deciduum and a volume of approximately 0.5 $\mu$l is expelled containing approximately 1000 cells. The micropipette is withdrawn and the incision is sutured shut. After an additional 3–4 days, the mother is sacrificed, and individual embryos are removed, fixed and analyzed for the presence and phenotype of cells derived from the injected neural crest cells.

To identify the progeny of the injected cells, it is necessary to have a means of distinguishing them from surrounding cells of the host embryo. This may be done as follows: rat neural crest cells are injected into a mouse embryo (following suitable immunosuppression of the mother or using a genetically immunodeficient strain such as the SCID strain of mice), the injected cells are identified by endogenous markers such as Thy1 or major histocompatibility complex (MHC) antigens using monoclonal antibodies specific for the rat Thy1 or MHC antigens. Alternatively, an exogenous genetic marker is introduced into the cells prior to their transplantation as a means of providing a marker on or in the injected cells. This is as follows: neural crest cells in culture are incubated with a suspension of replication-defective, helper-free retrovirus particles harboring the lacZ gene, at a titer of $10^5$–$10^6$ pfu/ml in the presence of 8 $\mu$l/ml polybrene for four hours. The cells are then washed several times with fresh medium and prepared for injection as described above. The harvested embryos are then assayed for expression of $\beta$-galactosidase by whole mount staining according to standard procedures. The blue cells (indicating expression of the lacZ gene) will correspond to the progeny of the injected neural crest cells. This procedure can be applied to any tissue or any stage of development in any animal suitable for transplantation studies. Following whole-mount staining, embryos bearing positive cells are embedded in freezing medium and sectioned at 10–20 $\mu$m on a cryostat. Sections containing blue cells are selected, and then counterstained for markers of mature neurons and glia using specific antibodies, according to standard techniques, and immunoperoxidase or alkalinephosphatase histochemistry. The identification of lacZ$^+$ (blue) cells expressing neuronal or glial markers indicates that the progeny of the injected neural crest cells have differentiated appropriately. Thus, this technique provides a means of identifying mammalian neural crest stem cells through transplantation studies to reveal the function of said stem cells.

Having described the preferred embodiments of the present invention, it will appear to those ordinarily skilled in the art that various modifications may be made to the disclosed embodiments, and that such modifications are intended to be within the scope of the present invention.

What is claimed is:

1. A method for obtaining an isolated population of mammalian neural crest stem cells, said method comprising:

a) contacting an embryonic neural tube with a first culture medium and a first substrate to allow the migration of neural crest cells from said neural tube onto said first substrate;

b) preparing a suspension comprising a population of emigrated neural crest cells and c) isolating a population of neural crest stem cells by contacting at least a portion of said neural crest cell suspension with a second culture medium and said first or a second substrate which permits self-renewal of one or more neural crest stem cells in said population, wherein said neural crest stem cells are capable of self-renewal in a feeder cell-independent culture medium and express low-affinity nerve growth factor receptor (LNGFR) and nestin, but do not express glial fibrillary acidic protein (GFAP), wherein at least one cell of said neural crest stem cell population is capable of differentiation to a peripheral nervous system neuronal cell that does not express LNGFR or nestin but does express neurofilament-160, and wherein at least one cell of said neural crest stem cell population is capable of differentiation to a peripheral nervous system glial cell that expresses LNGFR, nestin and GFAP.

2. The method of claim 1, wherein said first and second substrates comprise fibronectin.

3. The method of claim 1, wherein said first and second substrates comprise poly-D-lysine in combination with fibronectin.

4. A method according to claim 1, wherein said neural crest stem cells do not express sulfatide, myelin protein $P_o$, peripherin, high PSA-NCAM or neurofilament.

5. A method for obtaining an isolated population of neural crest stem cells from a mammalian tissue comprising:

a) preparing a suspension comprising a population of cells from said mammalian tissue, b) isolating said population of neural crest stem cells by contacting said cell suspension with a first culture medium and a first substrate which permit self-renewal of neural crest stem cells, wherein said neural crest stem cells are capable of self-renewal in a feeder cell-independent culture medium and express low-affinity nerve growth factor receptor (LNGFR) and nestin, but do not express glial fibrillary acidic protein (GFAP), wherein at least one cell of said neural crest stem cell population is capable of differentiation to a peripheral nervous system neuronal cell that does not express LNGFR or nestin but does express neurofilament-160, and wherein at least one cell of said neural crest stem cell population is capable of differentiation to a peripheral nervous system glial cell that expresses LNGFR, nestin and GFAP.

6. A method according to claim 5, wherein said neural crest stem cells do not express sulfatide, myelin protein $P_o$, peripherin, high PSA-NCAM or neurofilament.

7. A method according to claim 5 wherein said mammalian tissue comprises the neural tube.

8. The method of claim 5, wherein said first and second substrates comprise fibronectin.

9. The method of claim 5, wherein said first and second substrates comprise poly-D-lysine in combination with fibronectin.

10. A method for obtaining an isolated population of mammalian neural crest stem cells from a mammalian tissue, said method comprising:

a) preparing a suspension comprising cells from said mammalian tissue, b) contacting said suspension with a first antibody capable of forming a first complex with the low-affinity nerve growth factor receptor on said neural crest stem cell; and c) isolating the first complex formed from said contacting to form a population of neural crest stem cells, wherein said neural crest stem cells are capable of self-renewal in a feeder cell-independent culture medium and express low-affinity nerve growth factor receptor (LNGFR) and nestin, but do not express glial fibrillary acidic protein (GFAP), wherein at least one of said neural crest stem cell population is capable of differentiation to a peripheral nervous system neuronal cell that does not express LNGFR or nestin but does express neurofilament-160, and wherein at least one cell of said neural stem cell population is capable of differentiation to a peripheral nervous system glial cell that expresses LNGFR, nestin and GFAP.

11. The method according to claim 10 wherein said isolating further comprises forming a second complex by contacting said first complex with a reagent which specifically binds said first antibody in said first complex.

12. A method according to claim 11 wherein said reagent contains a fluorescent label and said isolating further comprises separating said second complex, if formed, by fluorescence-activated cell sorting.

13. A method according to claim 11 wherein said reagent comprises a second antibody capable of forming said second complex.

14. A method according to claim 13 wherein said reagent contains a fluorescent label and said isolating further comprises separating said second complex, if formed, by fluorescence-activated cell sorting.

15. A method according to claim 10, wherein said neural crest stem cells do not express sulfatide, myelin protein $P_o$, peripherin, high PSA-NCAM or neurofilament.

16. A method according to claim 10 wherein said mammalian tissue comprises the neural tube.

17. A method for obtaining an isolated population of mammalian peripheral nervous system neuronal cells in vitro comprising:

a) contacting an isolated population of mammalian neural crest stem cells with a culture medium comprising a factor permissive for peripheral nervous system neuronal cell differentiation, wherein said neural crest stem cells are capable of self-renewal in a feeder cell-independent culture medium, capable of differentiation to peripheral nervous system neuronal or glial cells and express low-affinity nerve growth factor receptor (LNGFR) and nestin but do not express glial fibrillary acidic protein (GFAP) and wherein said peripheral nervous system neuronal cells do not express LNGFR or nestin but do express neurofilament-160.

18. The method of claim 17 wherein said factor permissive for peripheral nervous system neuronal cell differentiation is a substrate comprising poly-D-lysine in combination with fibronectin.

19. A method for obtaining an isolated population of mammalian peripheral nervous system neuronal cells in vitro comprising:

a) contacting an isolated population of mammalian neural crest stem cells with a culture medium comprising a factor permissive for peripheral nervous system glial cell differentiation, wherein said neural crest stem cells are capable of self-renewal in a feeder cell-independent culture medium, capable of differentiation to peripheral nervous system neuronal or glial cells and express low-affinity nerve growth factor receptor (LNGFR) and nestin but do not express glial fibrillary acidic protein (GFAP) and wherein said peripheral nervous system glial cells express LNGFR, nestin, and GFAP.

20. The method of claim 19 wherein said factor permissive for peripheral nervous system glial cell differentiation is a substrate comprising fibronectin.

21. The method of claim 19 wherein said factor permissive for peripheral nervous system glial cell differentiation comprises forskolin and serum.

* * * * *